US007083782B2

(12) United States Patent
Liu et al.

(10) Patent No.: US 7,083,782 B2
(45) Date of Patent: *Aug. 1, 2006

(54) METHOD OF TREATMENT USING INTERFERON-TAU

(75) Inventors: Chih-Ping Liu, San Francisco, CA (US); Lorelie H. Villarete, Alameda, CA (US)

(73) Assignee: Pepgen Corporation, Alameda, CA (US)

(*) Notice: Subject to any disclaimer, the term of this patent is extended or adjusted under 35 U.S.C. 154(b) by 75 days.

This patent is subject to a terminal disclaimer.

(21) Appl. No.: 10/824,710

(22) Filed: Apr. 14, 2004

(65) Prior Publication Data

US 2005/0142109 A1 Jun. 30, 2005

Related U.S. Application Data

(60) Provisional application No. 60/552,279, filed on Mar. 10, 2004.

(51) Int. Cl.
*A61K 38/21* (2006.01)
(52) U.S. Cl. .................................... 424/85.4
(58) Field of Classification Search ............... 424/85.4, 424/85.7, 85.2
See application file for complete search history.

(56) References Cited

U.S. PATENT DOCUMENTS

| 5,705,363 | A |   | 1/1998  | Imakawa        |
|-----------|---|---|---------|----------------|
| 5,906,816 | A |   | 5/1999  | Soos et al.    |
| 5,958,402 | A |   | 9/1999  | Bazer et al.   |
| 6,036,949 | A |   | 3/2000  | Richards et al.|
| 6,060,450 | A | * | 5/2000  | Soos et al. ............ 514/12 |
| 6,083,919 | A |   | 7/2000  | Johnson et al. |
| 6,372,206 | B1|   | 4/2002  | Soos et al.    |
| 6,403,562 | B1|   | 6/2002  | Johnson et al. |
| 6,942,854 | B1|   | 9/2005  | Soos et al.    |
| 2002/0013452 | A1 | | 1/2002  | Johnson et al. |
| 2003/0012766 | A1 | | 1/2003  | Soos et al.    |
| 2003/0049277 | A1 | | 3/2003  | Sokawa et al.  |
| 2003/0130486 | A1 | | 7/2003  | Villarete et al. |
| 2003/0219405 | A1 | | 11/2003 | Sokawa et al.  |
| 2004/0013643 | A1 | | 1/2004  | Mach           |

FOREIGN PATENT DOCUMENTS

| WO | WO 90/09806 | 9/1990 |
| WO | WO 94/10313 | 5/1994 |
| WO | WO 96/28183 | 9/1996 |
| WO | WO 97/33607 | 9/1997 |
| WO | WO 00/78266 | 12/2000 |

OTHER PUBLICATIONS

Li et al (World Journal of Gastroenterology 10:620-625, 2004).*
van Roon et al (Journal of Rheumatology 30:648-51, abstract only cited).*
Soos et al (Journal of Immunology 169:2231-22235, 2002).*
Alexenko, A.P., et al., *Journal of Interferon and Cytokine Research* 17:769-779, (1997).
Brod, S.A., et al., *Journal of Neuroimmunology* 58:61-69, (1995).
Brod, S.A., et al., *Diabetologia* 41:1227-1232, (1998).
Brod, S.A., *Journal of Interferon and Cytokine Research* 19:841-852, (1999).
Khan, O.A., et al., *Mult Scler* 4(2):63-69, (1998).
Mujtaba, M.G., et al., *Cell Immunol* 186(2):94-102, (1998).
Nakajima, A., et al., *Journal of Interferon and Cytokine Research* 22:397-402, (2002).
Pontzer, C.H., et al., *Biochem Biophys* 152(2):801-807, (1988).
Pontzer, C.H., *Cancer Research* 51:5304-5307, (1991).
Soos, J.M., et al., *Journal of Interferon and Cytokine Research* 15:39-45, (1995).
Soos, J.M., et al., *Journal of Neuroimmunology* 75:43-50, (1997).
Soos, J.M., et al., *The Journal of Immunology* 169:2231-2235, (2002).
van Boxel-Dezaire, A.H.H., et al., *Ann Neurol* 45:695-703, (1999).

(Continued)

Primary Examiner—Mary E. Mosher
(74) *Attorney, Agent, or Firm*—Judy M. Mohr; Perkins Coie LLP

(57) ABSTRACT

Methods of treating an autoimmune condition, a viral infection, or a condition of cellular proliferation by administering IFNτ are described. More specifically, a method of up-regulating the IL-10 level in patients afflicted with an autoimmune condition, a viral infection, or a condition of cellular proliferation by administering IFNτ is described. IFNτ is administered at a dose sufficient to achieve an up-regulation of IL-10 in the blood, relative to the IL-10 level in the absence of IFNτ.

6 Claims, 16 Drawing Sheets

OTHER PUBLICATIONS

Chaouat, G., et al., *J Immunology* 154(9):4261-4268, (1995).
Mujtaba, M.G., et al., *J Neurol* 75(1-2):35-42, (1997).
Olek, M.J., et al., *Neurology* 56(Suppl 3):A76, (2001).
Kappos, L., et al., *J Neurol* 251(Suppl 5):V/57-V/64, (2004).
Killestein, J. and Polman, C.H., *Current opinion in Neurology* 18:253-260, (2005).
Tuo, W., et al., *J Interferon and Cytokine Research* 19:179-187, (1999).

* cited by examiner

SEQUENCE LISTING

<160> NUMBER OF SEQ ID NOS: 4

<210> SEQ ID NO 1
<211> LENGTH: 516
<212> TYPE: DNA
<213> ORGANISM: Ovis aries

<400> SEQUENCE: 1

```
tgctacctgt cgcgaaaact gatgctggac gctcgagaaa atttaaaact gctggaccgt    60
atgaatcgat tgtctccgca cagctgcctg caagaccgga aagacttcgg tctgccgcag   120
gaaatggttg aaggtgacca actgcaaaaa gaccaagctt tcccggtact gtatgaaatg   180
ctgcagcagt cttcaacct gttctacact gaacattctt cggccgcttg ggacactact    240
cttctagaac aactgtgcac tggtctgcaa cagcaactgg accatctgga cacttgccgt   300
ggccaggtta tgggtgaaga agactctgaa ctgggtaaca tggatccgat cgttactgtt   360
aaaaaatatt tccagggtat ctacgactac ctgcaggaaa aaggttactc tgactgcgct   420
tgggaaatcg tacgcgttga atgatgcgg gccctgactg tgtcgactac tctgcaaaaa    480
cggttaacta aatgggtgg tgacctgaat tctccg                              516
```

<210> SEQ ID NO 2
<211> LENGTH: 172
<212> TYPE: PRT
<213> ORGANISM: Ovis aries

<400> SEQUENCE: 2

```
Cys Tyr Leu Ser Arg Lys Leu Met Leu Asp Ala Arg Glu Asn Leu Lys
 1               5                  10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
                85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
    130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

<210> SEQ ID NO 3
<211> LENGTH: 172
<212> TYPE: PRT
<213> ORGANISM: Artificial
<220> FEATURE:
<223> OTHER INFORMATION: recombinant IFNtau based on Ovis aries sequence

<400> SEQUENCE: 3

```
Cys Tyr Leu Ser Glu Arg Leu Met Leu Asp Ala Arg Glu Asn Leu Lys
 1               5                  10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45
```

```
Gln Lys Asp Gln Ala Phe Pro Val Leu Tyr Glu Met Leu Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Leu Asp His Leu
                85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

<210> SEQ ID NO 4
<211> LENGTH: 516
<212> TYPE: DNA
<213> ORGANISM: Artificial
<220> FEATURE:
<223> OTHER INFORMATION: recombinant IFNtau based on Ovis aries sequence

<400> SEQUENCE: 4

```
tgctacctgt cggagcgact gatgctggac gctcgagaaa atttaaaact gctggaccgt      60
atgaatcgat tgtctccgca cagctgcctg caagaccgga aagacttcgg tctgccgcag     120
gaaatggttg aaggtgacca actgcaaaaa gaccaagctt tcccggtact gtatgaaatg     180
ctgcagcagt ctttcaacct gttctacact gaacattctt cggccgcttg ggacactact     240
cttctagaac aactgtgcac tggtctgcaa cagcaactgg accatctgga cacttgccgt     300
ggccaagtta tgggtgaaga agactctgaa ctgggtaaca tggatccgat cgttactgtt     360
aaaaaatatt tccagggtat ctacgactac ctgcaggaaa aaggttactc tgactgcgct     420
tgggaaatcg tacgcgttga aatgatgcgg gccctgactg tgtcgactac tctgcaaaaa     480
cggttaacta aaatgggtgg tgacctgaat tctccg                               516
```

METHOD OF TREATMENT USING INTERFERON-TAU

This application claims the benefit of U.S. Provisional Application No. 60/552,279 filed Mar. 10, 2004, incorporated herein by reference in its entirety.

FIELD OF THE INVENTION

The present invention relates to pharmaceutical compositions containing interferon-tau and methods of uses thereof. More particularly, the invention relates to methods of stimulating production of interleukin-10 (IL-10) for treating conditions that benefit from an elevated IL-10 serum levels, by administering interferon-tau (IFNτ) in a dose sufficient to increase serum IL-10.

BACKGROUND OF THE INVENTION

Interferon-tau (hereinafter "IFNτ" or "interferon-τ") was discovered originally as a pregnancy recognition hormone produced by the trophectoderm of ruminant conceptuses (Imakawa, K. et al, *Nature*, 330:377–379, (1987); Bazer, F. W. and Johnson, H. M., *Am. J. Repro. Immunol.*, 26:19–22, (1991)). The distribution of the IFNτ gene is restricted to ruminants, including cattle, sheep, and goats, (Alexenko, A. P. et al., *J. Interferon and Cytokine Res.*, 19:1335–1341, (1999)) but has been shown to have activity in cells belonging to other species including humans and mice (Pontzer, C. H. et al., *Cancer Res.*, 51:5304–5307, (1991); Alexenko, A. P. et al., *J. Interferon and Cytokine Res.*, 20:817–822, (2000)). For example, IFNτ has been demonstrated to possess antiviral, (Pontzer, C. H. et al., *Biochem. Biophys. Res. Commun.*, 152:801–807, (1988)), antiproliferative, (Pontzer, C. H., et al., 1991) and immunoregulatory activities (Assal-Meliani, A., *Am. J. Repro. Immunol.*, 33:267–275 (1995)).

While IFNτ displays many of the activities classically associated with type I IFNs, such as interferon-α and interferon-β, considerable differences exist between IFNτ and the other type I IFNs. The most prominent difference is the role of IFNτ in pregnancy in ruminant species. The other IFNs have no similar activity in pregnancy recognition. Also different is viral induction. All type I IFNs, except IFNτ, are induced readily by virus and dsRNA (Roberts, et al, *Endocrine Reviews*, 13:432 (1992)). Induced IFN-α and IFN-β expression is transient, lasting approximately a few hours. In contrast, IFNτ synthesis, once induced, is maintained over a period of days (Godkin, et al., *J. Reprod. Fert.*, 65:141 (1982)). On a per-cell basis, 300-fold more IFN-τ is produced than other type I IFNs (Cross, J. C. and Roberts, R. M., *Proc. Natl. Acad. Sci. USA* 88:3817–3821 (1991)).

Another difference lies in the amino acid sequences of IFNτ and other type I interferons. The percent amino acid sequence similarity between the interferons $α_{2b}$, $β_1$, $ω_1$, γ, and τ are summarized in the table below.

|              | rHuIFN$α_{2b}$ | rHuIFN$β_1$ | rHuIFN$_1ω_1$ | rHuIFN$_γ$ | rOvIFN$_τ$ |
|---|---|---|---|---|---|
| rHuIFN$α_{2b}$ |      | 33.1 | 60.8 | 11.6 | 48.8 |
| rHuIFN$β_1$    | 33.1 |      | 33.1 | 12.2 | 33.8 |
| rHuIFN$ω_1$    | 60.8 | 33.1 |      | 10.2 | 54.9 |
| rHuIFN$_γ$     | 11.6 | 12.2 | 10.2 |      | 10.2 |
| rOvIFN$_τ$     | 48.8 | 33.8 | 54.9 | 10.2 |      |

Sequence comparison determined from the following references:
Taniguchi et al., Gene, 10(1): 11 (1980).
Adolf et al., Biochim. Biophys. Acta, 1089(2): 167 (1991).
Streuli et al., Science, 209: 1343 (1980).
Imakawa et al., Nature, 330: 377 (1987).

Recombinant ovine IFNτ is 48.8 percent homologous to IFN$α_{2b}$ and 33.8 percent homologous to IFN$β_1$. Because of this limited homology between IFNτ and IFNα and between IFNτ and IFNβ, it cannot be predicted whether or not IFNτ would behave in the same manner as IFNα or IFNβ when administered orally. IFNτ is also reported to have a low receptor binding affinity for type I receptors on human cells (Brod, S., *J. Interferon and Cytokine Res.*, 18:841 (1999); Alexenko, A. et al., *J. Interferon and Cytokine Res.*, 17:769 (1997)). Additionally, the fact that IFNτ is a non-endogeneous human protein generates the potential for systemic neutralizing antibody formation when IFNτ is introduced into the human body (Brod, S., *J. Interferon and Cytokine Res.*, 18:841 (1999). These differences between IFNτ and the other interferons make it difficult to predict whether IFNτ when administered to a human will provide a therapeutic benefit. Teachings in the art relating to oral administration of IFNα, IFNβ, or any other non-tau interferon, fail to provide a basis for drawing any expectations for IFNτ.

One limiting factor in the use of IFNτ, as well as proteins and polypeptides in general, is related to biodistribution, as affected by protein interaction with plasma proteins and blood cells, when given parenterally. The oral route of administration is even more problematic due to proteolysis in the stomach, where the acidic conditions can destroy the molecule before reaching its intended target. For example, polypeptides and protein fragments, produced by action of gastric and pancreatic enzymes, are cleaved by exo- and endopeptidases in the intestinal brush border membrane to yield di- and tri-peptides. If proteolysis by pancreatic enzymes is avoided, polypeptides are subject to degradation by brush border peptidases. Polypeptides or proteins that might survive passage through the stomach are subject to metabolism in the intestinal mucosa where a penetration barrier prevents entry into cells. For this reason, much effort has been focused on delivering proteins to the oral-pharyngeal region in the form of a lozenge or solution held in the oral cavity for a period of time.

The role of cytokines in various diseases and correlations between cytokine blood levels with disease onset and severity is of interest to the medical community. Recent research shows that multiple sclerosis patients with low serum levels of IL-10 have more pronounced disability than patients with a higher IL-10 level (Petereit, H. F., *J. Neurological Sciences,* 206:209 (2003). It has also been reported that down-regulation of IL-12 may be beneficial in treating patients with multiple sclerosis (Tuohy, V. et al., *J. Neuroimmunol.,* 111 (1–2):55 (2000)). A link between interferon-gamma and multiple sclerosis is also reported in the literature (Moldovan, I. R. et al., *J. Neuroimmunol.,* 141(1–2):132 (2003)).

SUMMARY OF THE INVENTION

Accordingly, it is an object of the invention to provide a method of modulating cytokine levels in a human subject.

It is another object of the invention to provide a method of treating an autoimmune condition in a subject by modulating the subject's serum cytokine levels in such a way to alleviate symptoms, inhibit progression of the condition, and/or facilitate resolution of the condition.

It is another object of the invention to provide a method of treating a viral infection in a subject by modulating the subject's serum cytokine levels in such a way to alleviate symptoms, inhibit progression of the infection, and/or facilitate resolution of the infection.

It is another object of the invention to provide a method of treating a condition associated with cellular proliferation in a subject by modulating the subject's serum cytokine levels in such a way to alleviate symptoms, inhibit continued cellular proliferation, and/or facilitate resolution of the proliferation.

In one aspect, the invention includes a method of achieving these objects by administering, to a patient suffering from or at risk of continued progression of a disease condition, a dose of interferon-tau sufficient to modulate selected serum cytokine levels, relative to baseline serum cytokine levels of that patient or of a model patient population.

In another aspect the invention includes a method for up-regulating the blood interleukin-10 (IL-10) level in a human subject, comprising orally administering interferon-tau (IFNτ) to the subject at a daily dosage of greater than $5 \times 10^8$ Units to produce an initial measurable increase in the subject's blood IL-10 level, relative to the blood IL-10 level in the subject in the absence of interferon-tau administration. Oral administration of IFNτ to the subject continues on a regular basis of at least several times per week, independent of changes in the subject's blood IL-10 level, until a desired clinical endpoint is achieved.

In one embodiment, the IFNτ is ovine IFNτ or bovine IFNτ. Exemplary ovine IFNτ sequences are identified as SEQ ID NO:2 or SEQ ID NO:3.

In another embodiment, IFNτ is orally administered to the intestinal tract of the subject.

When treating a subject suffering from an autoimmune condition, in one embodiment, the desired clinical endpoint is alleviation of the subject's symptoms. Exemplary autoimmune conditions include multiple sclerosis, Type I diabetes mellitus, rheumatoid arthritis, lupus erythematosus, psoriasis, Myasthenia Gravis, Graves' disease, Hashimoto's thyroiditis, Sjogren's syndrome, ankylosing spondylitis, and inflammatory bowel disease.

In another embodiment, IFNτ is orally administered to a subject suffering from a viral infection. IFNτ is administered until a clinical endpoint is reached, such as a reduction in symptoms associated with the viral infection or a reduction in blood viral titer. The viral infection can result from DNA virus or an RNA virus. Exemplary viral infections include hepatitis A, hepatitis B, hepatitis C, non-A, non-B, non-C hepatitis, Epstein-Barr viral infection, HIV infection, herpes virus (EB, CML, herpes simplex), papilloma, poxvirus, picorna virus, adeno virus, rhino virus, HTLV I, HTLV II, and human rotavirus.

In another embodiment, IFNτ is orally administered for treatment of a disorder characterized by cellular proliferation. IFNτ is administered until a clinical endpoint is reached, such as a reduction in symptoms associated with the disorder. Exemplary cellular proliferation conditions include human lung large cell carcinoma, human colon adenocarcinoma, human malignant melanoma, human renal adenocarcinoma, human promyelocytic leukemia, human T cell lymphoma, human cutaneous T cell lymphoma, human breast adenocarcinoma, and steroid sensitive tumors.

In other embodiment, administration of IFNτ is combined with administration of a second therapeutic agent, simultaneously or sequentially. Exemplary second therapeutic agents incude anti-viral agents, anti-cancer agents, and agents suitable for treatment of autoimmune disorders.

In another aspect, the invention includes a method of slowing the progression of multiple sclerosis in a subject by orally administering IFNτ to the subject at a daily dosage of greater than about $5 \times 10^8$ Units to produce an initial measurable increase in the subject's blood IL-10 level, relative to the blood IL-10 level in the subject in the absence of interferon-tau administration, and continuing to orally administer IFNτ to the subject on a regular basis of at least several times per week, independent of changes in the subject's blood IL-10 level.

In yet another aspect, the invention includes a method of reducing the risk of relapse in a subject suffering from multiple sclerosis, comprising orally administering IFNτ to the subject at a daily dosage of greater than about $5 \times 10^8$ Units to produce an initial measurable increase in the subject's blood IL-10 level, relative to the blood IL-10 level in the subject in the absence of interferon-tau administration, and continuing to orally administer IFNτ to the subject on a regular basis of at least several times per week, independent of changes in the subject's blood IL-10 level.

In still another aspect, a method of treating an autoimmune condition in a subject is described. The method comprises administering to the subject IFNτ in an amount sufficient to produce an initial measurable increase in the subject's blood IL-10 level, relative to the blood IL-10 level in the subject in the absence of interferon-tau administration; ceasing administration of IFNτ for a selected period of time during which the subject's blood IL-10 level remains increased relative to the blood IL-10 level in the subject in the absence of IFNτ administration; and resuming administration of IFNτ.

These and other objects and features of the invention will be more fully appreciated when the following detailed description of the invention is read in conjunction with the accompanying drawings.

BRIEF DESCRIPTION OF THE SEQUENCES

Figure 1A:
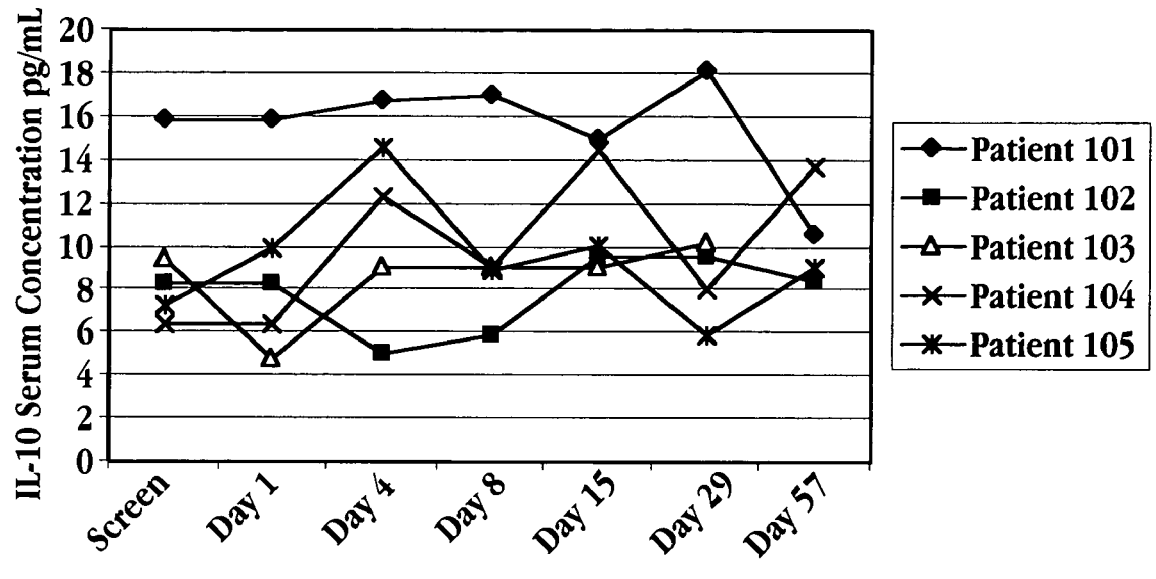
FIGS. 1A–1C are graphs showing the IL-10 serum level, in pg/mL, in human patients suffering from multiple sclerosis and treated orally with IFNτ, as a function of time, in days, for patient groups I, II, and III treated daily with 0.2 mg IFNτ (FIG. 1A), 0.6 mg IFNτ (FIG. 1B), and 1.8 mg IFNτ (FIG. 1C) from days 1–29.

SEQ ID NO:1 is the nucleotide sequence of a synthetic gene encoding ovine interferon-τ (IFNτ).

SEQ ID NO:2 corresponds to an amino acid sequence of mature ovine interferon-τ (IFNτ; oTP-1; GenBank Accession No. Y00287; PID g1358).

SEQ ID NO:3 corresponds to an amino acid sequence of mature ovine IFNτ, where the amino acid residues at positions 5 and 6 of the sequence are modified relative to the sequence of SEQ ID NO:2.

SEQ ID NO:4 is a synthetic nucleotide sequence encoding the protein of SEQ ID NO:3.

DETAILED DESCRIPTION OF THE INVENTION

I. Definitions

Interferon-tau, abbreviated as IFNτ or interferon-τ, refers to any one of a family of interferon proteins having at least one characteristic from each of the following two groups of characteristics: (i) (a) anti-luteolytic properties, (b) anti-viral properties, (c) anti-cellular proliferation properties; and (ii) about 45 to 68% amino acid homology with α-interferons and greater than 70% amino acid homology to known IFNτ sequences (e.g., Ott, et al., *J. Interferon Res.,* 11:357 (1991); Helmer, et al., *J. Reprod. Fert.,* 79:83 (1987); Imakawa, et al., *Mol. Endocrinol.,* 3:127 (1989); Whaley, et al., *J. Biol. Chem.,* 269:10846 (1994); Bazer, et al., WO 94/10313 (1994)). Amino acid homology can be determined using, for example, the LALIGN program with default parameters. This program is found in the FASTA version 1.7 suite of sequence comparison programs (Pearson and Lipman, *PNAS,*85:2444 (1988); Pearson, *Methods in Enzymology,* 183:63 (1990); program available from William R. Pearson, Department of Biological Chemistry, Box 440, Jordan Hall, Charlottesville, Va.). IFNτ sequences have been identified in various ruminant species, including but not limited to, cow (*Bovine* sp., Helmer S. D., *J. Reprod. Fert.,* 79:83 (1987); Imakawa, K., *Mol. Endocrinol.,* 119:532 (1988)), sheep (*Ovine* sp.), musk ox (*Ovibos* sp.), giraffe (*Giraffa* sp., GenBank Accession no. U55050), horse (*Equus caballus*), zebra (*Equus burchelli,* GenBank Accession no. NC005027), hippopotamus (*Hippopotamus* sp.), elephant (*Loxodonta* sp.), llama (*Llama glama*), goat (*Capra* sp., GenBank Accession nos. AY357336, AY357335, AY347334, AY357333, AY357332, AY357331, AY357330, AY357329, AY357328, AY357327), and deer (*Cervidae* sp.). The nucleotide sequences of IFNτ for many of these species are reported in public databases and/or in the literature (see, for example, Roberts, R. M. et al., *J. Interferon and Cytokine Res.,* 18:805(1998), Leaman D. W. et al., *J. Interferon Res.,* 12:1 (1993), Ryan, A. M. et al., *Anim. Genet.,* 34:9 (1996)). The term "interferon-tau" intends to encompass the interferon-tau protein from any ruminant species, exemplified by those recited above, that has at least one characteristic from each of the following two groups of characteristics listed above.

Ovine IFNτ (OvIFNτ) refers to a protein having the amino acid sequence as identified herein as SEQ ID NO:2, and to proteins having amino acid substitutions and alterations such as neutral amino acid substitutions that do not significantly affect the activity of the protein, such as the IFNτ protein identified herein as SEQ ID NO:3. More generally, an ovine IFNτ protein is one having about 80%, more preferably 90%, sequence homology to the sequence identified as SEQ ID NO:2. Sequence homology is determined, for example, by a strict amino acid comparison or using one of the many programs commercially available.

Treating a condition refers to administering a therapeutic substance effective to reduce the symptoms of the condition and/or lessen the severity of the condition.

Oral refers to any route that involves administration by the mouth or direct administration into the stomach or intestines, including gastric administration.

Intestine refers to the portion of the digestive tract that extends from the lower opening of the stomach to the anus, composed of the small intestine (duodenum, jejunum, and ileum) and the large intestine (ascending colon, transverse colon, descending colon, sigmoid colon, and rectum).

"Measurable increase in blood IL-10 lever" refers to a statistically meaningful increase in blood (serum and/or blood-cell) levels of interleukin-10, typically at least a 20% increase, more preferably a 25% increase, over pre-treatment levels measured under identical conditions. Methods for measuring IL-10 levels in the blood are described herein using a commercially-available enzyme-linked immunosorbent assay (ELISA) kit. A fold-increase is determined by dividing the value at timepoint x by the screening or baseline value. A percent increase is determined by finding the difference between the value at timepoint x and the screening or baseline value; dividing this difference by the screening or baseline value; and multiplying the quotient by 100.

"Measurable decrease in blood IL-12 level" refers to a statistically meaningful increase in blood (serum and/or blood-cell) levels of interleukin-12, typically at least a 20% increase, more preferably a 25% increase, over pre-treatment levels measured under identical conditions. Methods for measuring IL-12 levels in the blood are described herein using a commercially-available enzyme-linked immunosorbent assay (ELISA) kit. A fold-increase is determined by dividing the value at timepoint x by the screening or baseline value. A percent increase is determined by finding the difference between the value at timepoint x and the screening or baseline value; dividing this difference by the screening or baseline value, and multiplying the quotient by 100.

"Maintaining interferon-gamma blood level" or "no substantial decrease in interferon-gamma blood level" refers to no statistically meaningful change in blood (serum and/or blood-cell) level of interferon-gamma. Methods for measuring interferon-gamma levels in the blood are described herein using a commercially-available enzyme-linked immunosorbent assay (ELISA) kit.

A "daily dosage of greater than $5 \times 10^8$ Units" refers to an amount of IFNτ sufficient to provide more than about $5 \times 10^8$ antiviral Units of protein, where the antiviral activity of IFNτ is measured using a standard cytopathic effect inhibition assay, such as that described in the Methods section below. It will be appreciated that the amount (i.e., mg) of protein to provide a daily dosage of greater than $5 \times 10^8$ Units will vary according to the specific antiviral activity of the protein.

II. Interferon-τ Compositions and Method of Treatment

A. Interferon-τ

The first IFNτ to be identified was ovine IFNτ (IFNτ), as a 18–19 kDa protein. Several isoforms were identified in conceptus (the embryo and surrounding membranes) homogenates (Martal, J., et al., *J. Reprod. Fertil.* 56:63–73 (1979)). Subsequently, a low molecular weight protein released into conceptus culture medium was purified and shown to be both heat labile and susceptible to proteases (Godkin, J. D., et al., *J. Reprod. Fertil.* 65:141–150 (1982)). IFNτ was originally called ovine trophoblast protein-one (oTP-1) because it was the primary secretory protein initially produced by trophectoderm of the sheep conceptus during the critical period of maternal recognition in sheep. Subsequent experiments have determined that IFNτ is a pregnancy recognition hormone essential for establishment of the physiological response to pregnancy in ruminants, such as sheep and cows (Bazer, F. W., and Johnson, H. M., *Am. J. Reprod. Immunol.* 26:19–22 (1991)).

An IFNτ cDNA obtained by probing a sheep blastocyst library with a synthetic oligonucleotide representing the N-terminal amino acid sequence (Imakawa, K. et al, *Nature,* 330:377–379, (1987)) has a predicted amino acid sequence that is 45–55% homologous with IFN-αs from human, mouse, rat, and pig and 70% homologous with bovine IFN-αII, now referred to as IFN-Ω. Several cDNA sequences have been reported which may represent different isoforms (Stewart, H. J., et al., *Mol. Endocrinol.* 2:65 (1989); Klemann, S. W., et al., *Nuc. Acids Res.* 18:6724 (1990); and Charlier, M., et al., *Mol. Cell Endocrinol.* 76:161–171 (1991)). All are approximately 1 kb with a 585 base open reading frame that codes for a 23 amino acid leader sequence and a 172 amino acid mature protein. The predicted structure of IFNτ as a four helical bundle with the amino and carboxyl-termini in apposition further supports its classification as a type I IFN (Jarpe, M. A., et al., *Protein Engineering* 7:863–867 (1994)).

| Overview of the Interferons | | | | |
|---|---|---|---|---|
| Aspects | Type I | Type I | Type I | Type II |
| Types | α & ω | β | τ | γ |
| Produced by: | leukocyte | fibroblast | trophoblast | lymphocyte |
| Antiviral | + | + | + | + |
| Antiproliferative | + | + | + | + |
| Pregnancy Signaling | − | − | + | − |

While IFNτ displays some of the activities classically associated with type I IFNs (see Table, above), considerable differences exist between it and the other type I IFNs. The most prominent difference is its role in pregnancy, detailed above. Also different is viral induction. All type I IFNs, except IFNτ, are induced readily by virus and dsRNA (Roberts, R. M., et al., *Endocrin. Rev.* 13:432–452 (1992)). Induced IFN-α and IFN-β expression is transient, lasting approximately a few hours. In contrast, IFNτ synthesis, once induced, is maintained over a period of days (Godkin, et al., 1982). On a per-cell basis, 300-fold more IFNτ is produced than other type I IFNs (Cross, J. C., and Roberts, R. M., *Proc. Natl. Acad. Sci. USA* 88:3817–3821 (1991)).

Other differences may exist in the regulatory regions of the IFNτ gene. For example, transfection of the human trophoblast cell line JAR with the gene for bovine IFNτ resulted in antiviral activity while transfection with the bovine IFN-Ω gene did not. This implies unique transacting factors involved in IFNτ gene expression. Consistent with this is the observation that while the proximal promoter region (from 126 to the transcriptional start site) of IFNτ is highly homologous to that of IFN-α and IFN-β; the region from −126 to −450 is not homologous and enhances only IFNτ expression (Cross, J. C., and Roberts, R. M., *Proc. Natl. Acad. Sci. USA* 88:3817–3821 (1991)). Thus, different regulatory factors appear to be involved in IFNτ expression as compared with the other type I IFNs.

The 172 amino acid sequence of ovine-IFNτ is set forth, for example, in U.S. Pat. No. 5,958,402, and its homologous bovine-IFNτ sequence is described, for example, in Helmer et al., *J. Reprod. Fert.,* 79:83–91 (1987) and Imakawa, K. et al., *Mol. Endocrinol.,* 3:127 (1989). The sequences of ovine-IFNτ and bovine-IFNτ from these references are hereby incorporated by reference. An amino acid sequence of ovine IFNτ is shown herein as SEQ ID NO:2.

1. Isolation of IFNτ

IFNτ may be isolated from conceptuses collected from pregnant sheep and cultured in vitro in a modified minimum essential medium as described by Godkin, J. D., et al., *J. Reprod. Fertil.* 65:141–150 (1982) and Vallet, J. L., et al., *Biol. Reprod.* 37:1307 (1987). The IFNτ may be purified from the conceptus cultures by ion exchange chromotography and gel filtration. The homogeneity of isolated IFNτ may be assessed by sodium dodecyl sulfate polyacrylamide gel electrophoresis (Maniatis, T., et al., in *MOLECULAR CLONING: A LABORATORY MANUAL*, Cold Spring Harbor Laboratory, Cold Spring Harbor, N.Y. (1982); Ausubel, F. M., et al., in *CURRENT PROTOCOLS IN MOLECULAR BIOLOGY*, John Wiley & Sons, Inc., Media, Pa. (1988)), and determination of protein concentration in purified IFNτ samples may be performed using the bicinchoninic (BCA) assay (Pierce Chemical Co., Rockford, Ill.; Smith, P. K., et al., *Anal. Biochem.* 150:76 (1985)).

2. Recombinant Production of IFNτ

Recombinant IFNτ protein may be produced from any selected IFNτ polynucleotide fragment using a suitable expression system, such as bacterial or yeast cells. The isolation of IFNτ nucleotide and polypeptide sequences is described in PCT publication WO/94/10313, which is incorporated by reference herein.

To make an IFNτ expression vector, an IFNτ coding sequence (e.g., SEQ ID NOS:1 or 4) is placed in an expression vector, e.g., a bacterial expression vector, and expressed according to standard methods. Examples of suitable vectors include lambda gt11 (Promega, Madison Wis.); pGEX (Smith, P. K. et al., *Anal. Biochem.* 150:76 (1985)); pGEMEX (Promega); and pBS (Strategene, La Jolla Calif.) vectors. Other bacterial expression vectors containing suitable promoters, such as the T7 RNA polymerase promoter or the tac promoter, may also be used. Cloning of the IFNτ synthetic polynucleotide into a modified pIN III omp-A expression vector is described in the Materials and Methods.

For the studies described herein, the IFNτ coding sequence present in SEQ ID NO:4 was cloned into a vector, suitable for transformation of yeast cells, containing the methanol-regulated alcohol oxidase (AOX) promoter and a Pho1 signal sequence. The vector was used to transform *P. pastoris* host cells and transformed cells were used to express the protein according to the manufacturer's instructions (Invitrogen, San Diego, Calif.).

Other yeast vectors suitable for expressing IFNτ for use with methods of the present invention include 2 micron plasmid vectors (Ludwig, D. L. et al., *Gene,* 132:33 (1993)), yeast integrating plasmids (Shaw, K. J. et al., *DNA,* 7:117 (1988)), YEP vectors (Shen, L. P. et al., *Sci. Sin.,* 29:856 (1986)), yeast centromere plasmids (YCps), and other vectors with regulatable expression (Hitzeman, R. A. et al., U.S. Pat. No. 4,775,622, issued Oct. 4, 1988; Rutter, W. J. et al., U.S. Pat. No. 4,769, 238, issued Sep. 6, 1988; Oeda, K. et al., U.S. Pat. No. 4,766,068, issued Aug. 23, 1988). Preferably, the vectors include an expression cassette containing an effective yeast promoter, such as the MFα1 promoter (Bayne, M. L. et al., *Gene* 66:235–244 (1988), GADPH promoter (glyceraldehyde-3-phosphate-dehydrogenase; Wu, D. A. et al., *DNA,* 10:201 (1991)) or the galactose-inducible GAL10 promoter (Ludwig, D. L. et al., *Gene,* 132:33 (1993); Feher, Z. et al., *Curr. Genet.,* 16:461 (1989)); Shen, L. P. et al., *Sci. Sin.,* 29:856 (1986)). The yeast transformation host is typically *Saccharomyces cerevisiae*, however, as illustrated above, other yeast suitable for transformation can be used as well (e.g., *Schizosaccharomyces pombe, Pichia pastoris* and the like).

Further, a DNA encoding an IFNτ polypeptide can be cloned into any number of commercially available vectors to generate expression of the polypeptide in the appropriate host system. These systems include the above described bacterial and yeast expression systems as well as the following: bacullrus expression (Reilly, P. R. et al., BACULOVIRUS EXPRESSION VECTORS: A LABORATORY MANUAL, (1992); Beames et al., *Biotechniques,* 11:378 (1991); Clontech, Palo Alto Calif.); plant cell expression, transgenic plant expression, and expression in mammalian cells (Clontech, Palo Alto Calif.; Gibco-BRL, Gaithersburg Md.). The recombinant polypeptides can be expressed as fusion proteins or as native proteins. A number of features can be engineered into the expression vectors, such as leader sequences which promote the secretion of the expressed sequences into culture medium. The recombinantly produced polypeptides are typically isolated from lysed cells or culture media. Purification can be carried out by methods known in the art including salt fractionation, ion exchange chromatography, and affinity chromatography. Immunoaffinity chromatography can be employed, as described above, using antibodies generated based on the IFNτ polypeptides.

In addition to recombinant methods, IFNτ proteins or polypeptides can be isolated from selected cells by affinity-based methods, such as by using appropriate antibodies. Further, IFNτ peptides (e.g. SEQ ID NOS:2 or 3) may be chemically synthesized using methods known to those skilled in the art.

B. Administration of IFNτ

In studies performed in support of the invention, IFNτ was administered to patient suffering from multiple sclerosis and to patients afflicted with hepatitis C. During the studies, the blood serum levels of the cytokines IL-10, IFN-γ, and IL-12 were monitored in each patient. These studies will now be described.

1. Administration of IFNτ to Humans Suffering from Multiple Sclerosis

Humans suffering from multiple sclerosis were enrolled in a trial for treatment with IFNτ. As described in Example 1, 15 patients were randomized into three treatment groups, summarized in Table 1.

TABLE 1

|  | Group I (n = 5) | Group II (n = 5) | Group III (n = 5) |
| --- | --- | --- | --- |
| IFNτ Oral Dose[1] | 0.2 mg/day (2 × 10$^7$ U) | 0.6 mg/day (6 × 10$^7$ U) | 1.8 mg/day (1.8 × 10$^8$ U) |
| Average Weight | 67.2 kg | 58.9 kg | 90.0 kg |
| Average Age | 30 | 34.5 | 47 |

[1] 1 mg IFNτ = 1 × 10$^8$ Units

Prior to treatment, blood samples were taken from each subject to determine a baseline serum cytokine concentration. After the blood draw on Day 1, each patient began treatment by taking the IFNτ orally in the appropriate dose. Treatment continued for 28 days and blood samples were taken from each patient on days 1, 4, 8, 15, 29, and 57 of the study. The samples were analyzed for IFNγ and IL-10 concentrations.

Figure 1B:
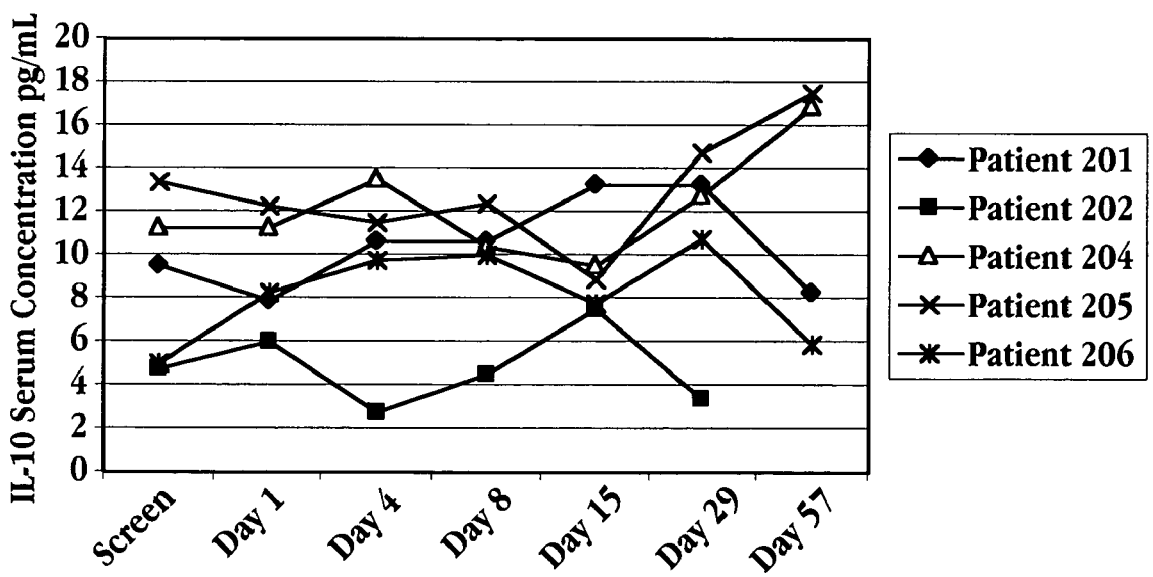
Figure 1C:
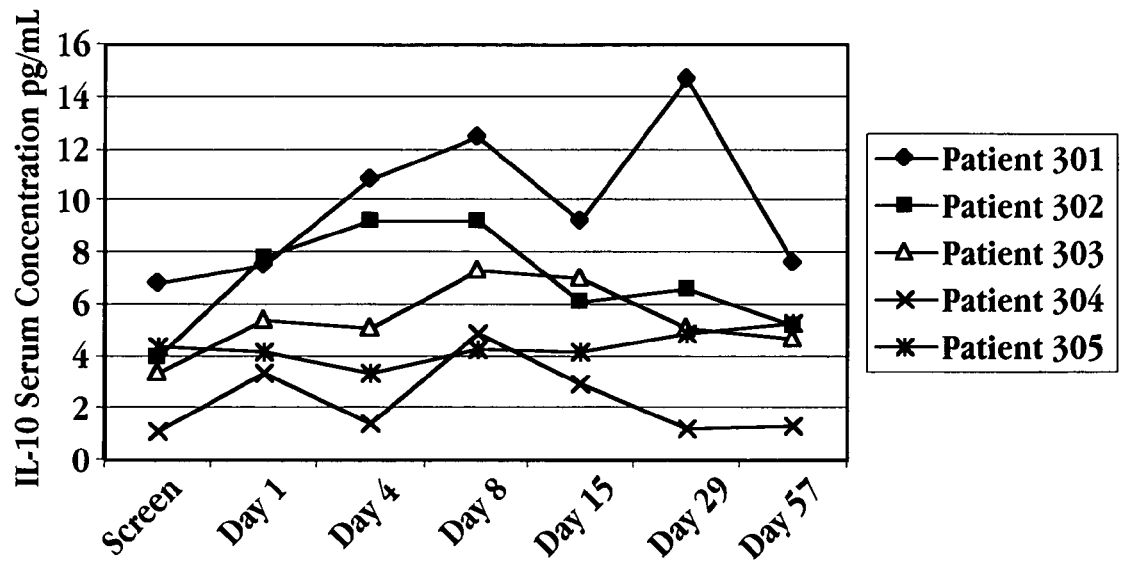

The IL-10 levels for the patients in Groups I, II, and III are shown in FIGS. 1A–1C, respectively. FIG. 1A shows serum IL-10 levels, in pm/mL, for the five patients in Group I. Three of the patients, patient numbers 103, 104, and 105, showed an increase in IL-10 level at Day 4, however the IL-10 levels decreased on the Day 8 reading in these patients. The IL-10 levels at Days 8 and 15 in Patient nos. 103 and 104 were not significantly changed from the level at Day 4. FIGS. 1B and 1C show the results for the patients in test Groups II and III, respectively. There is a suggestion of a slight increase in serum IL-10 levels after administration of IFNτ, particularly in the Group III patients.

Figure 1D:
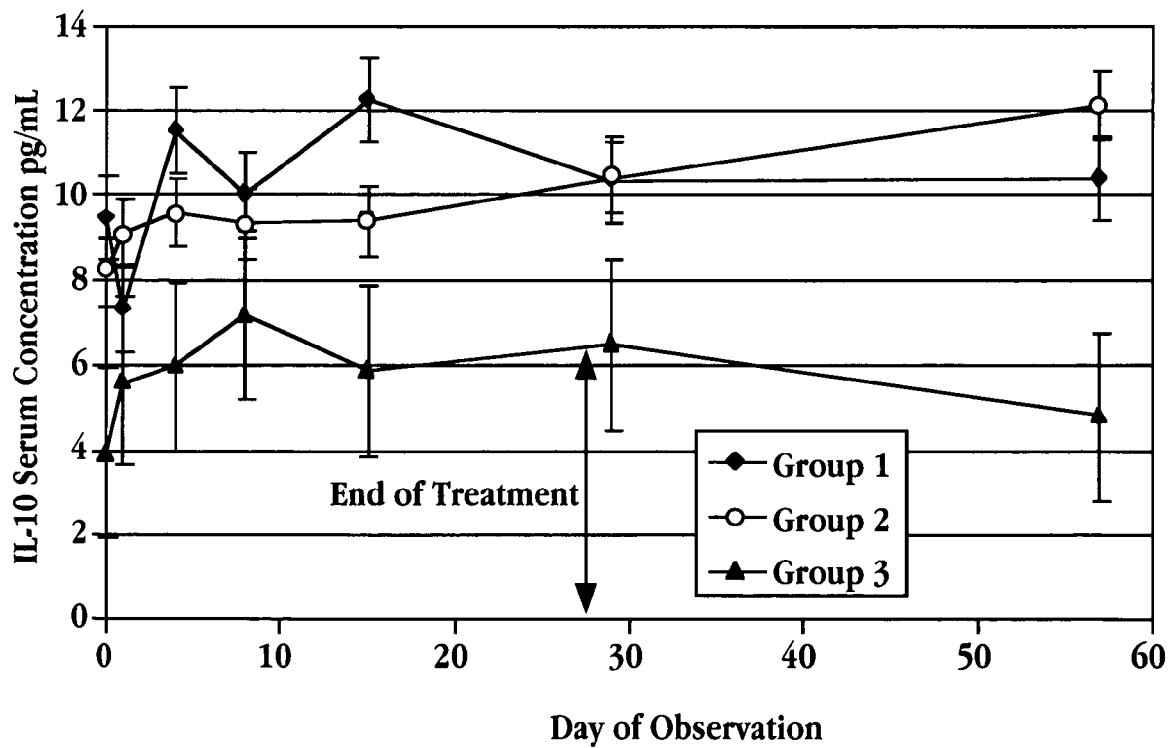
FIG. 1D is a graph showing the mean IL-10 serum level, in pg/mL, for the human patients in each of the test Groups I, II, and III treated daily with 0.2 mg IFNτ (diamonds, Group I), 0.6 mg IFNτ (squares, Group II), and 1.8 mg IFNτ (triangles, Group III) from days 1–29.

FIG. 1D shows the mean IL-10 serum levels, in pg/mL, for Groups I, II, and III. A slight upregulation of IL-10 in the test groups during the period of IFNτ dosing, between Days 2 and 28, however, the slight upregulation was not statistically significant, based on the statistical analysis set forth in Example 1. The small increase in IL-10 blood level continued in Groups I and II for a period of time after dosing with IFNτ was stopped on Day 28. The IL-10 serum levels at Day 57, which is 34 days after the last dose of IFNτ, remained above the baseline levels measured on Day 0 and Day 1. Thus, the invention contemplates a method of treating an autoimmune condition in a subject, where IFNτ is administered in an amount sufficient to produce an initial measurable increase in the subject's blood IL-10 level, relative to the blood IL-10 level in the subject in the absence of interferon-tau administration. Then, administration of IFτ is terminated for a selected period of time during which the subject's blood IL-10 level remains increased relative to the blood IL-10 level in the subject in the absence of interferon-tau administration. Administration of IFNτ may then resume as desired.

In this study, the blood levels of IFN-γ were also monitored. IFN-γ is a pro-inflammatory cytokine, and up-regulation of IFN-γ is correlated with increased discomfort in patients suffering from autoimmune conditions, such as multiple sclerosis and arthritis. During treatment of multiple sclerosis with interferon-beta (IFN-β), it has been reported that the frequency of IFN-γ-secreting cells increases during the first two months of IFN-β treatment, and this increase of IFN-γ serum levels possibly contributes to the prominent "flu-like" symptoms that patients experience during treatment with IFN-β. Thus, a method of treating autoimmune conditions where IL-10 levels are favorably up-regulated with no accompanying up-regulation of IFN-γ would be beneficial.

Figure 2A:
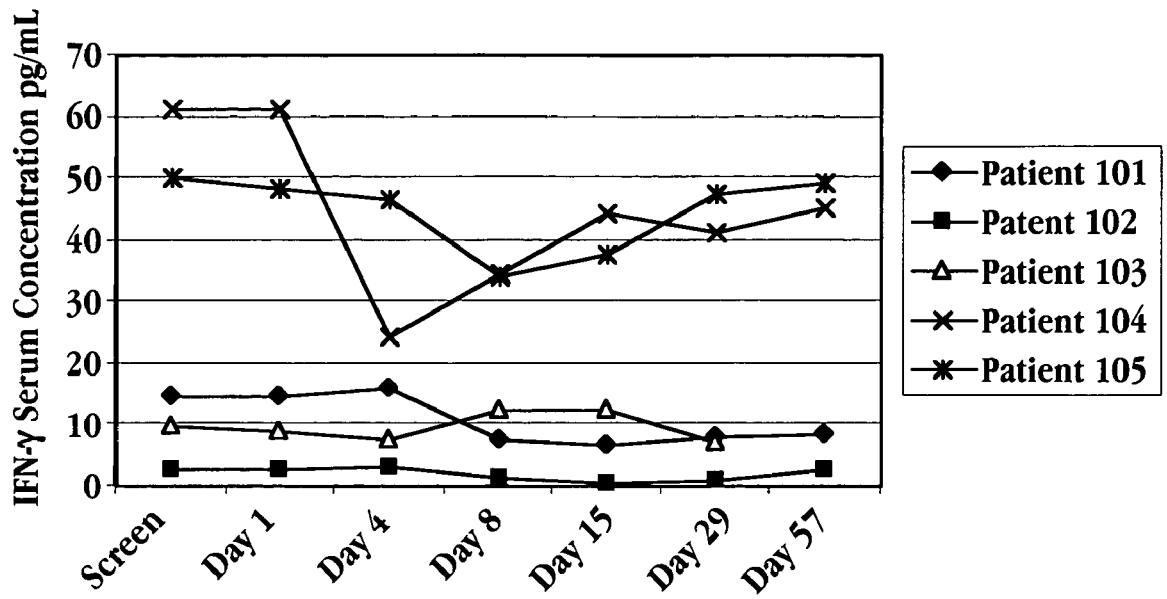
FIGS. 2A–2C are graphs showing the IFN-γ serum level, in pg/mL, in human patients suffering from multiple sclerosis and treated orally with IFNτ, as a function of time, in days, for patient groups I, II, and III treated daily with 0.2 mg IFNτ (FIG. 2A), 0.6 mg IFNτ (FIG. 2B), and 1.8 mg IFNτ (FIG. 2C) from days 1–29.

FIGS. 2A–2D show the IFN-γ blood levels, in pg/mL, for the patients in Groups I, II, and III, suffering from multiple sclerosis and treated orally with IFNτ. FIG. 2A shows the serum levels for the patients in Group I, treated with 0.2 mg IFNτ. Patient nos. 101, 102, 104, 105 each had a reduction in IFN-γ blood level during the course of treatment. The serum levels increased upon cessation of treatment at Day 28. The IFN-γ serum level in patient no. 103 did not increase, but remained essentially unchanged.

Figure 2B:
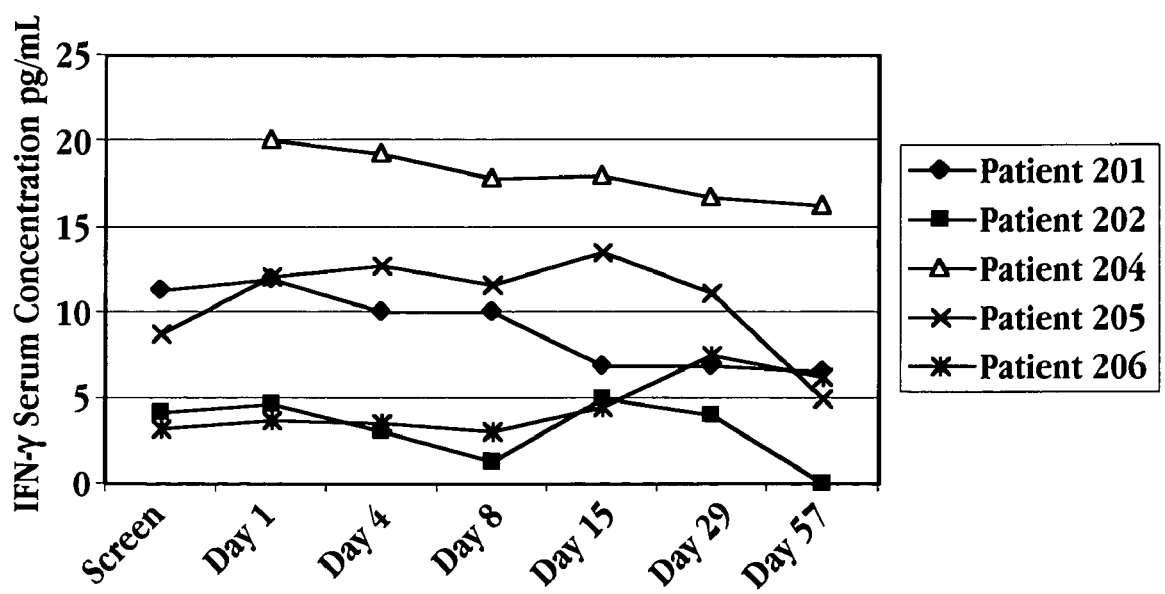
Figure 2C:
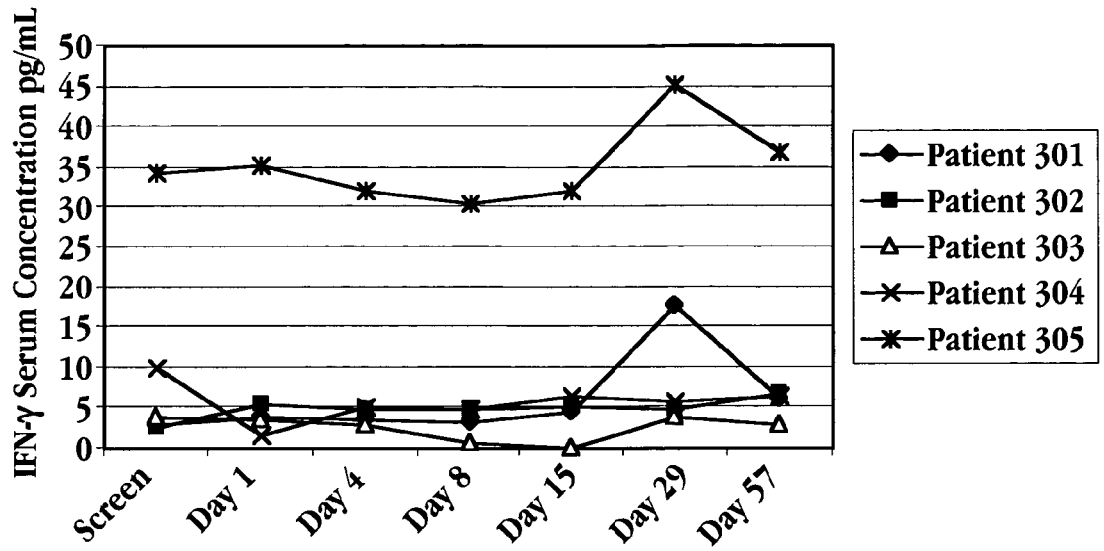

FIG. 2B shows the IFN-γ blood levels, in pg/mL, for the patients in Group II, and treated with 0.6 mg IFNτ daily. FIG. 2C shows the IFN-γ blood levels, in pg/mL, for the patients in Group III, and treated with 1.8 mg IFNτ daily. As noted above, the first dose of IFN-τ was taken after the blood draw on Day 1 and the final dose was taken on Day 28. Thus, the data points at Day 1 and "screen" are baseline levels for the individual patients. All patients in Groups II and III experienced either a reduction in IFN-γ serum levels or no meaningful change in IFN-γ serum level during treatment with IFN-γ.

Figure 2D:
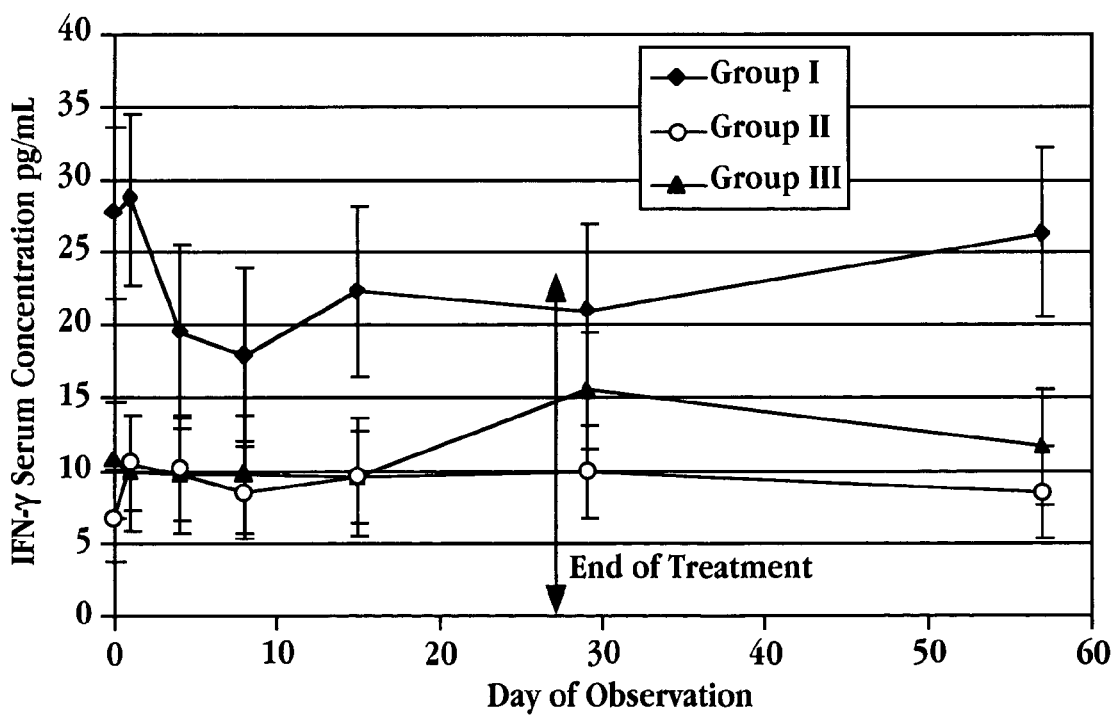
FIG. 2D is a graph showing the mean IFN-γ serum level, in pg/mL, for the human patients in each of the test Groups I, II, and III treated daily with 0.2 mg IFNτ (diamonds, Group I), 0.6 mg IFNτ (squares, Group II), and 1.8 mg IFNτ (triangles, Group III) from days 1–29.

FIG. 2D summarizes the mean blood level of IFN-γ, in pg/mL, for the patients in each of the test Groups I, II, and III. The decreasing trend of the IFN-γ blood levels is apparent, particularly when the higher doses of IFN-τ are administered (Group III).

Figure 3A:
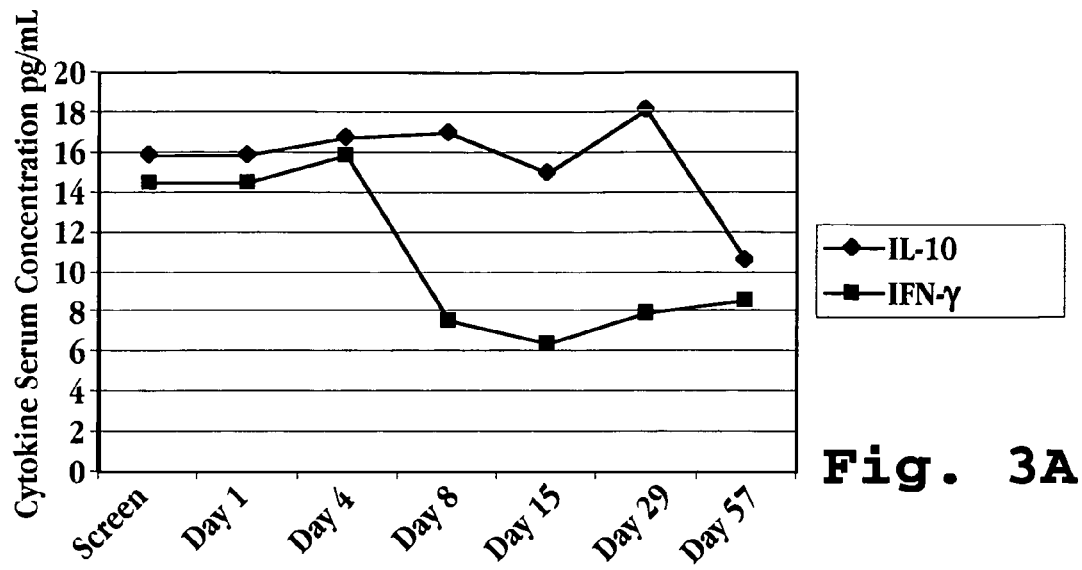
FIGS. 3A–3E show IL-10 (diamonds) and IFN-γ (squares) serum concentrations, both in pg/mL, for selected individual patients from the treatment Groups I, II, and III discussed with respect to FIGS. 1–2.

FIGS. 3A–3E show IL-10 (diamonds) and IFN-γ (squares) serum concentrations, both in pg/mL, for selected individual patients from the treatment Groups I, II, and III. FIG. 3A shows the cytokine production kinetics for patient number 101, in treatment Group I. The blood IL-10 level (diamonds) does not increase statistically during the treatment period. The IFN-γ blood level decreases during treatment with orally administered IFN-τ. The baseline levels of IL-10 and IFN-γ were 15.8 pg/mL and 14.5 pg/mL, respectively, to give an initial IL-10/IFN-γ ratio of 1.1. During treatment with IFN-τ, the IL-10/IFN-γ ratio increased to about 2.2, due to the decreasing IFN-γ blood level. The IL-10/IFN-γ ratio returned to the baseline ratio of about 1.1 at Day 57, about a month after treatment ended. Thus, during the period of treatment with IFN-τ, the IL-10/IFN-γ ratio was increased by about 100%.

Figure 3B:
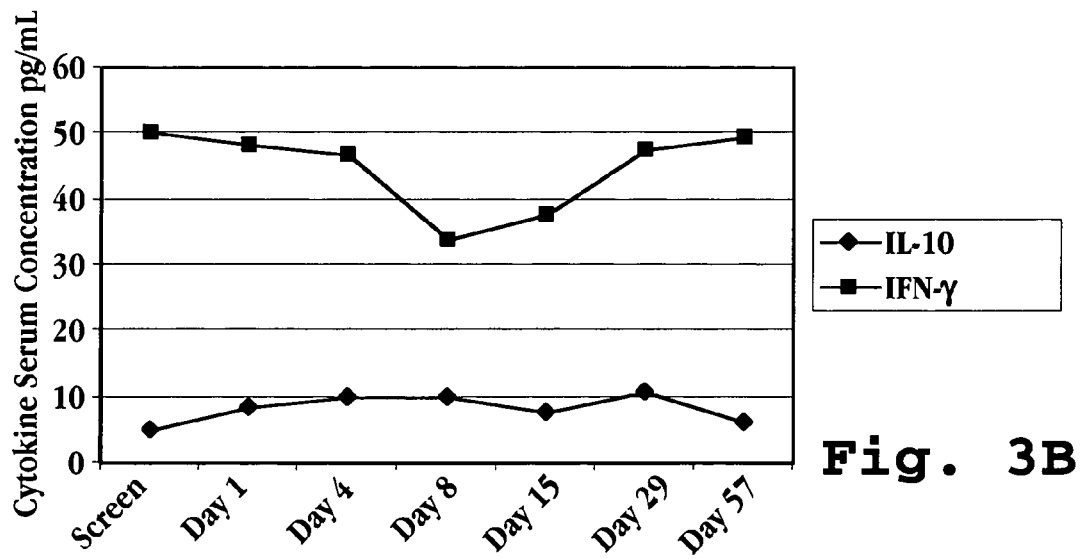

FIG. 3B shows the cytokine production kinetics for patient number 105, in treatment Group I. The baseline levels of IL-10 and IFN-γ were on average of 6.6 pg/mL and 49.2 pg/mL, respectively, to give an initial IL-10/IFN-γ ratio of 0.13. During treatment with IFN-τ, the IL-10/IFN-γ ratio increased to about 0.2–0.3, due to a decrease in IFN-γ blood level. The IL-10/IFN-γ ratio returned to the baseline ratio of about 0.12 at Day 57, about a month after treatment ended. Thus, treatment with IFNτ was effective to modulate the IL-10/IFN-γ ratio, increasing the ratio by more than 50%, more preferably by more than 80%.

Figure 3C:
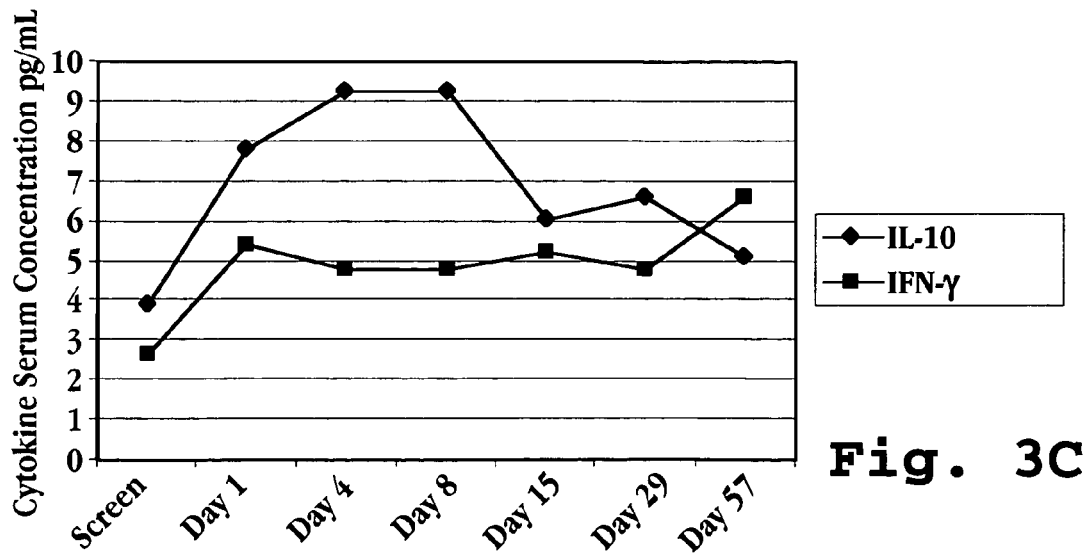

FIG. 3C shows the cytokine production kinetics for patient number 302, in treatment Group III. The baseline levels (taken as an average of Screen and Day 1) of IL-10 and IFN-γ were 5.8 pg/mL and 4.0 pg/mL, respectively, to give an initial IL-10/IFN-γ ratio of 1.45. During treatment with IFN-τ, the average IL-10 blood level (average of IL-10 levels on Days 4, 8, 15) was 7.7 pg/mL, which was not statistically different than the baseline IL-10 level (average of IL-10 blood levels at Screen and Day 1). The IFN-γ level remained substantially unchanged over the treatment period. The IL-10/IFN-γ ratio for this patient remained essentially unchanged.

Figure 3D:
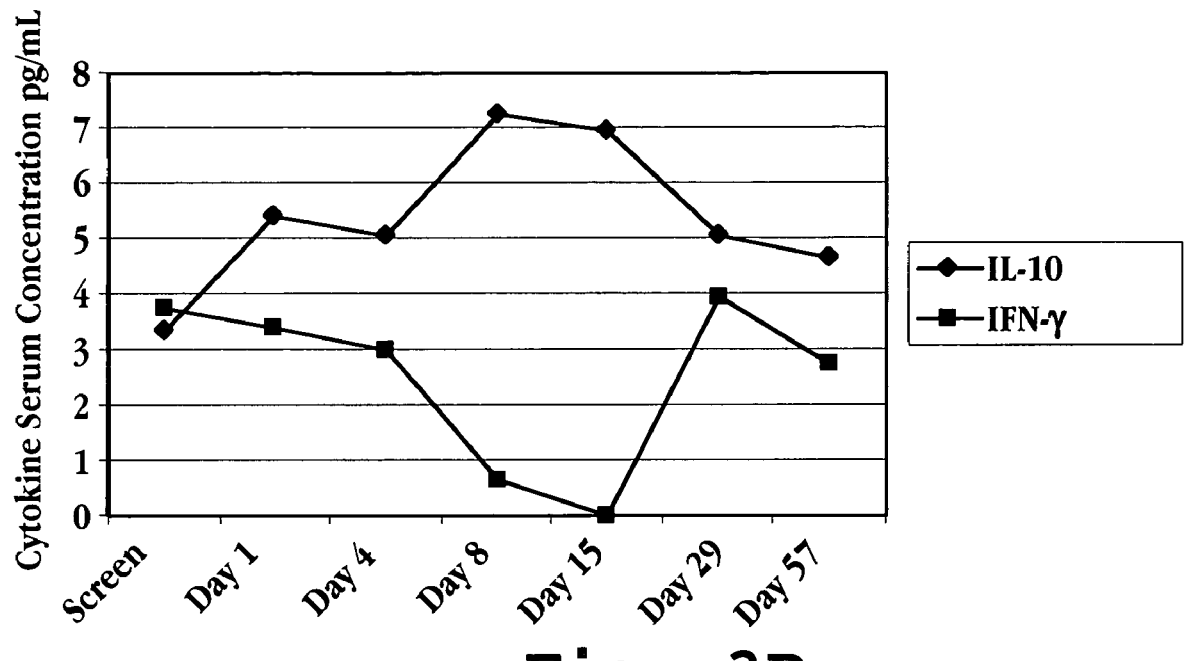

FIG. 3D shows the cytokine production kinetics for patient number 303, in treatment Group III. The baseline levels (taken as an average of Screen and Day 1) of IL-10 and IFN-γ were 4.4 pg/mL and 3.6 pg/mL, respectively, to give an initial IL-10/IFN-γ ratio of 1.2. During treatment with IFN-τ, due to a decrease in IFN-γ blood level, the IL-10/IFNγ ratio increased to about 11 on Day 8, with a return to the baseline ratio at Day 29.

Figure 3E:
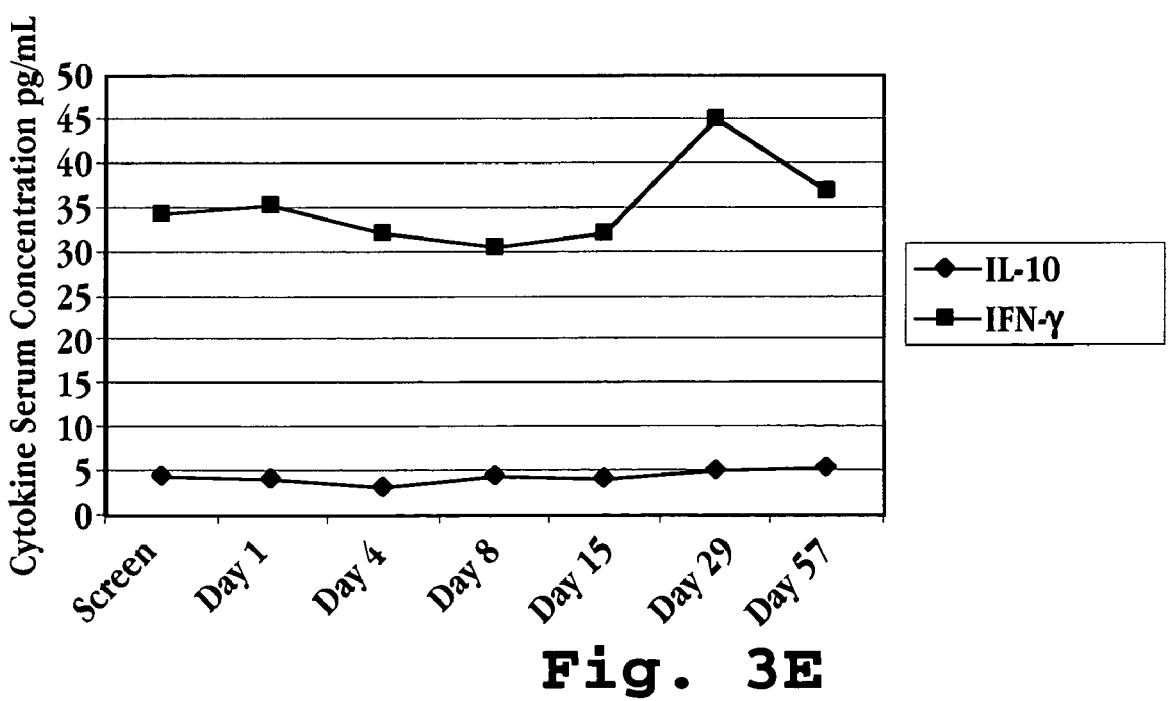

FIG. 3E shows the cytokine production kinetics for patient number 305 in treatment Group III. The baseline level (taken as an average of Screen and Day 1) of IL-10 and IFN-γ were 4.3 pg/mL and 34.8 pg/mL, respectively, to give an initial IL-10/IFN-γ ratio of 0.1. During treatment with IFN-τ, the IL-10 blood level was essentially constant; the IFN-γ blood level decreased slightly, to give an IL-10IFN-γ ratio increase by about 14%, to 0.14, on Day 8.

Thus, in another aspect, the invention provides a method of increasing IL-10/IFNγ ratio in subjects suffering from an autoimmune condition or a viral infection, comprising administering IFNτ to the subject in an amount effective to produce an initial measurable increase in the subject's blood IL-10 level, relative to the blood IL-10 level in the subject in the absence of interferon-tau administration, with (i) no substantial change in the subject's blood IFNγ level relative to the IFNγ level in the absence of IFNτ administration or (ii) a decrease in the subject's blood IFNγ level relative to the IFNγ level in the absence of IFNτ administration. The IL-10/IFN-γ ratio is increased by at least about 10%, preferably by about 25%, more preferably by about 40%, still more preferably by at least about 50%. In one embodiment, the IFNτ is ovine or bovine IFNτ. In another embodiment, the IFNτ is administered at a dose of greater than about $5 \times 10^8$ antiviral Units (U), more preferably, at a dose of $0.5 \times 10^9$ U or more, still more preferably at a dose of $1 \times 10^9$ U or more.

2. Administration to Humans Suffering from Hepatitis C

In another study, human patients infected with hepatitis C were recruited. The patients were divided into four test groups for treatment with oral IFNτ (SEQ ID NO:4). As described in Example 2, each subject in the test groups self-administered three times daily a controlled volume of a 1 mg/mL solution of IFNτ. Patients in Test Groups I, II, and III received a total daily dose of 1 mg IFNτ, 3 mg IFNτ, 9 mg IFNτ, and 15 mg IFNτ, respectively (1 mg IFNτ is approximately $1 \times 10^8$ antiviral Units). The treatment period lasted for 84 days, with the patients returning to the test clinic at defined intervals to provide a blood sample for analysis of the levels of IL-10 and IFN-γ. Monitoring continued for 169 days, 85 days after the end of treatment with IFNτ.

Figure 4A:
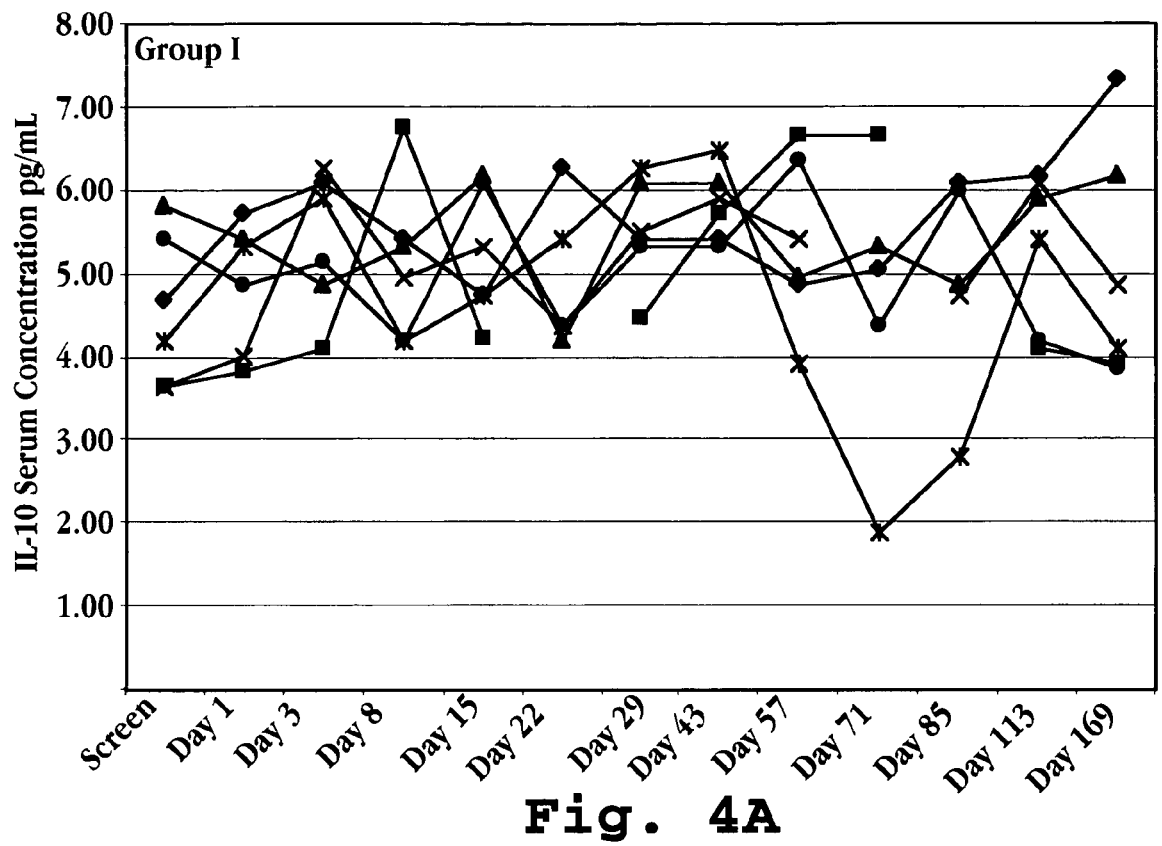
FIGS. 4A–4C are graphs showing the IL-10 serum level, in pg/mL, in human patients suffering from hepatitis C and treated orally with IFNτ, as a function of time, in days, for the six patients in Test Group I treated daily with 0.33 mg IFNτ three times daily (FIG. 4A), for the six patients in Test Group II treated daily with 1.0 mg IFNτ three times daily (FIG. 4B); and for the six patients in Test Group IIII treated daily with 3 mg IFNτ three times daily (FIG. 4C).
Figure 4B:
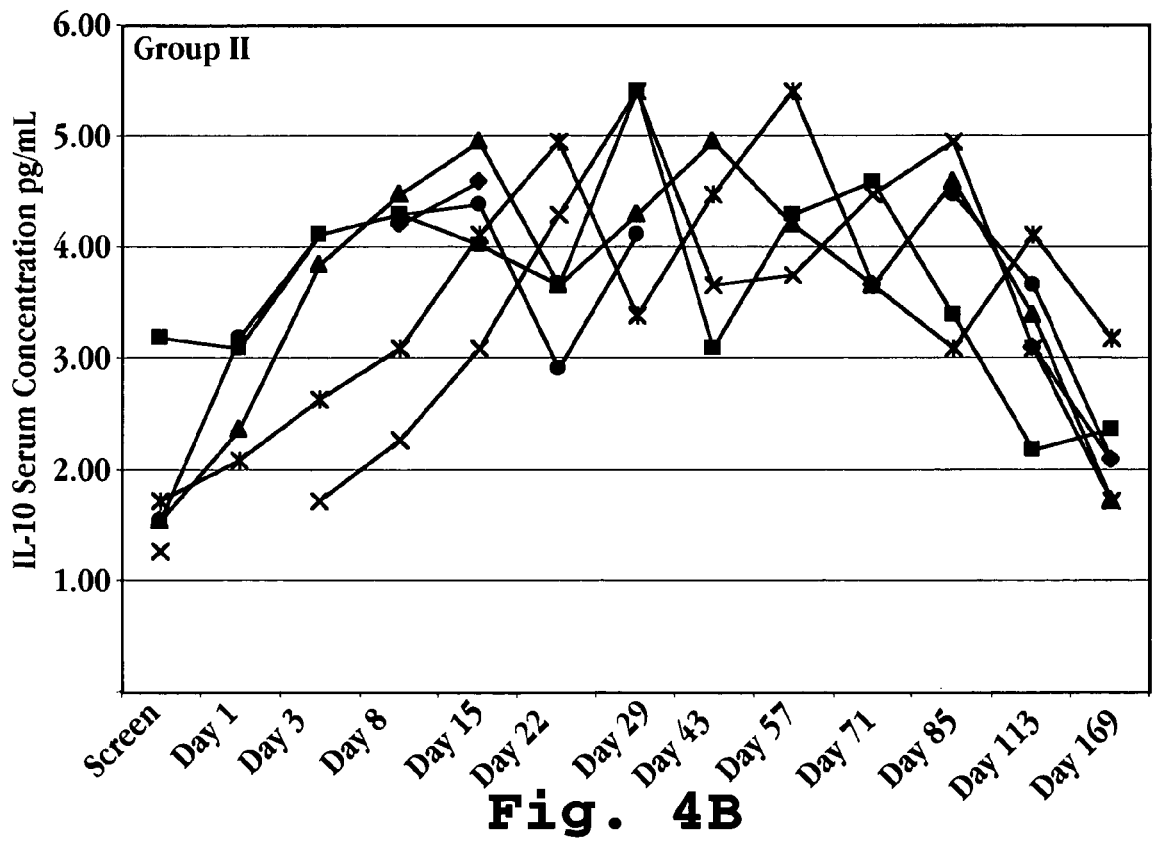
Figure 4C:
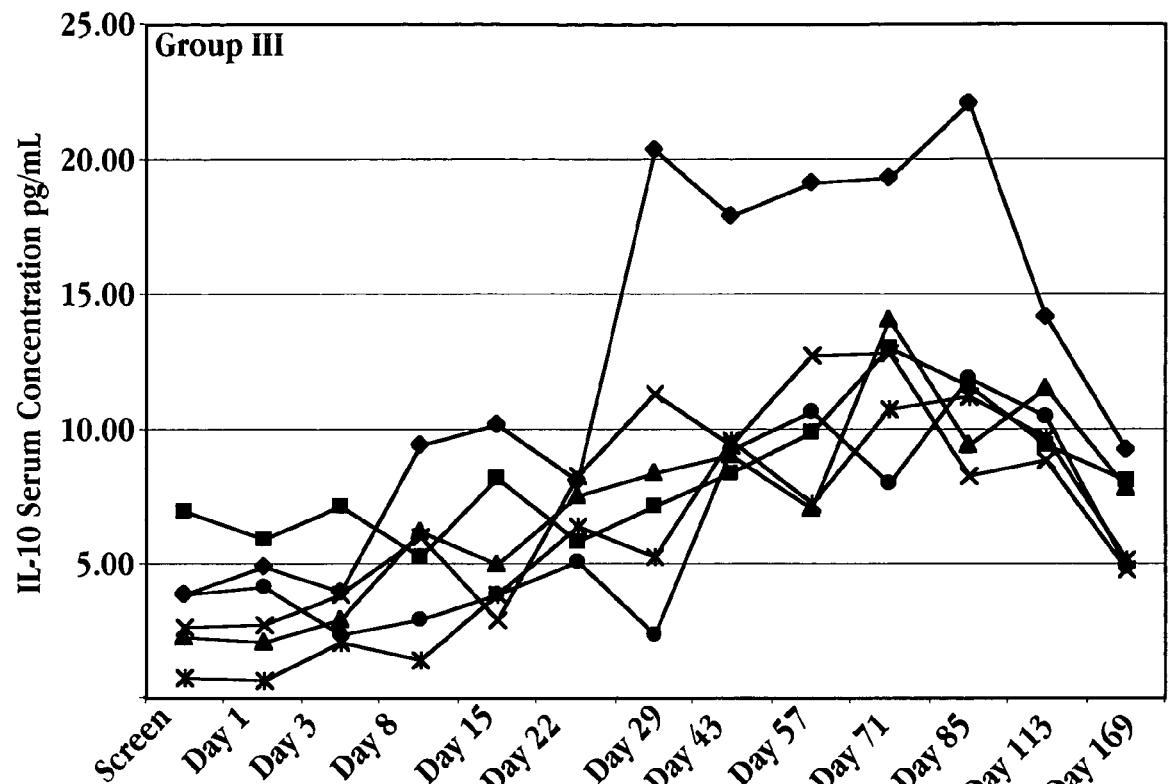

FIGS. 4A–4C are graphs showing the IL-10 serum level, in pg/mL, in the six patients in each of the test Groups I, II, and III. FIG. 4A shows the IL-10 levels for the six patients in Test Group I treated daily with 0.33 mg IFNτ three times daily, for a total daily dose of 1 mg ($1 \times 10^8$ U). The data for all patients shows a slight, though not statistically significant, trend toward increasing IL-10 levels.

FIG. 4B shows the data for the six patients in Test Group II, each treated daily with 1.0 mg IFNτ three times daily ($3 \times 10^8$ U/day) until Day 84. The data for all patients shows a more definite, yet not statistically significant, trend toward increasing IL-10 levels over the treatment period (Days 1–84). Upon cessation of IFNτ dosing, the IL-10 blood levels slowly approached baseline levels over the period of continued monitoring from Day 85–169.

FIG. 4C shows the IL-10 serum levels for the six patients in test Group III, treated daily with 3 mg IFNτ three times daily ($9 \times 10^8$ U/day) from Day 1 to Day 84. All patients had a statistically increased serum IL-10 level in response to dosing with IFNτ. Upon termination of IFNτ dosing, the IL-10 blood levels remained elevated for nearly 3 months.

Figure 4D:
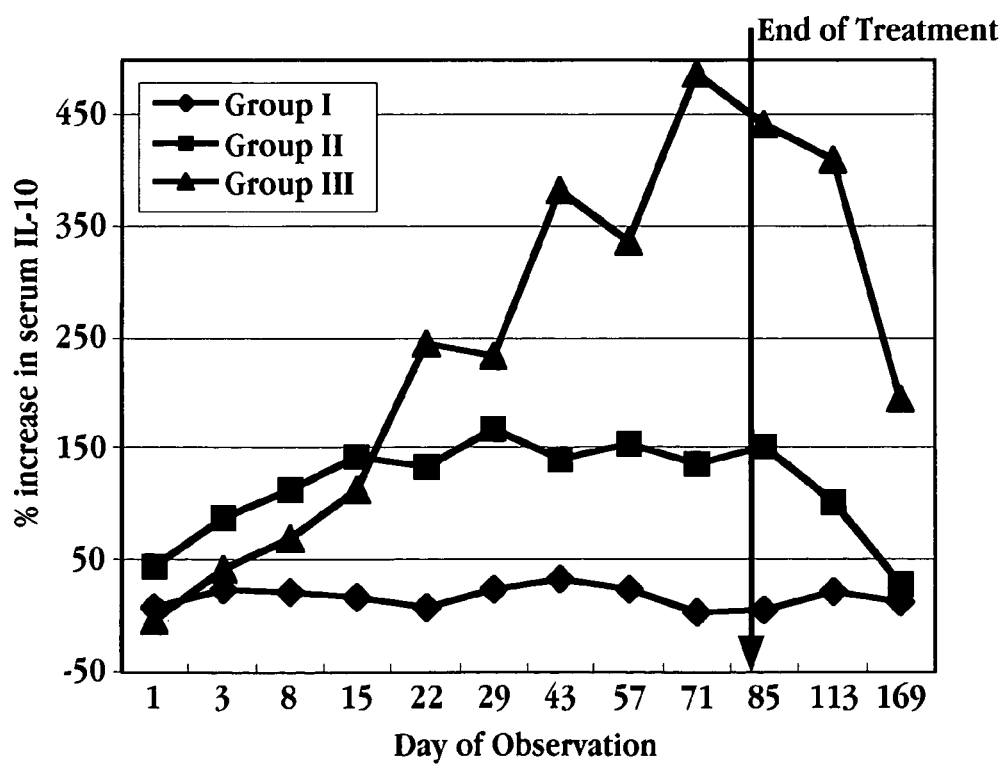
FIG. 4D is a summary plot for the test Groups I, II, and III in FIGS. 4A–4C, showing the percent increase in serum IL-10 levels as a function of time for test Group I (diamonds, 0.33 mg three times daily), Group II (squares, 1 mg three times daily), and Group III (triangles, 3 mg three times daily).

FIG. 4D is a summary plot of the IL-10 serum levels for the test Groups I, II, and III in FIGS. 4A–4C. FIG. 4D shows the percent increase in serum IL-10 levels as a function of time for test Group I (diamonds, 0.33 mg three times daily), Group II (squares, 1 mg three times daily), and Group III (triangles, 3 mg three times daily). The percent increase in serum IL-10 level as a function of dose is evident from the drawing, with the highest dose of 9 mg (3 mg three times daily; ($9 \times 10^8$ U/day) inducing an up-regulation of IL-10 of more than 100% within the first 15 days of treatment. A daily dose of 3 mg (test Group II, squares) stimulated IL-10 production to cause about a 150% increase by test Day 15. The 3 mg daily dose was sufficient to maintain the 150% increase for the 84 day test period.

FIG. 4D also illustrates the continued elevation in IL-10 levels, relative to baseline, pretreatment levels, during the period of days 85–169 when dosing of IFNτ had ceased. In test Group III (9 mg IFN-τ daily), the IL-10 level had not returned to baseline levels by day 169. Thus, a method of treating an autoimmune condition, particularly multiple sclerosis, psoriasis, rheumatoid arthritis and allergies, by administering to the subject IFNτ in an amount sufficient to produce an initial measurable increase in the subject's blood IL-10 level, relative to the blood IL-10 level in the subject in the absence of interferon-tau administration; ceasing administration of IFNτ for a selected period of time during which the subject's blood IL-10 level remains increased relative to the blood IL-10 level in the subject in the absence of IFNτ administration; and resuming administration of IFNτ when desired, such as when symptoms worsen, is contemplated. The amount of IFNτ sufficient to produce an initial measurable increase in the blood IL-10 level is greater than about $5 \times 10^8$ U/day, more preferably $0.5 \times 10^9$ U/day or more, still more preferably $1 \times 10^9$ U/day or more. The time period during which administration of IFNτ is ceased can vary according to the disease condition, but is readily determined from studies where the IL-10 levels of patients suffering from that disease condition are monitored during treatment with IFNτ and after termination of treatment with IFNτ. Results from such a study can be applied generally to other patients and provide recommended dosing patterns. Alternatively, the time period during which administration of IFNτ is ceased can be tracked for individual patients, by actual monitoring of IL-10 blood levels on a regular basis, e.g., weekly or twice weekly, during a period of non-treatment to determine when treatment should resume, or by a subjective indication of patient perception of symptoms. Treatment resumes when the IL-10 level approaches pre-treatment levels for that particular patient or for a model patient population, or when symptoms worsen for a particular patient being treated.

Figure 5A:
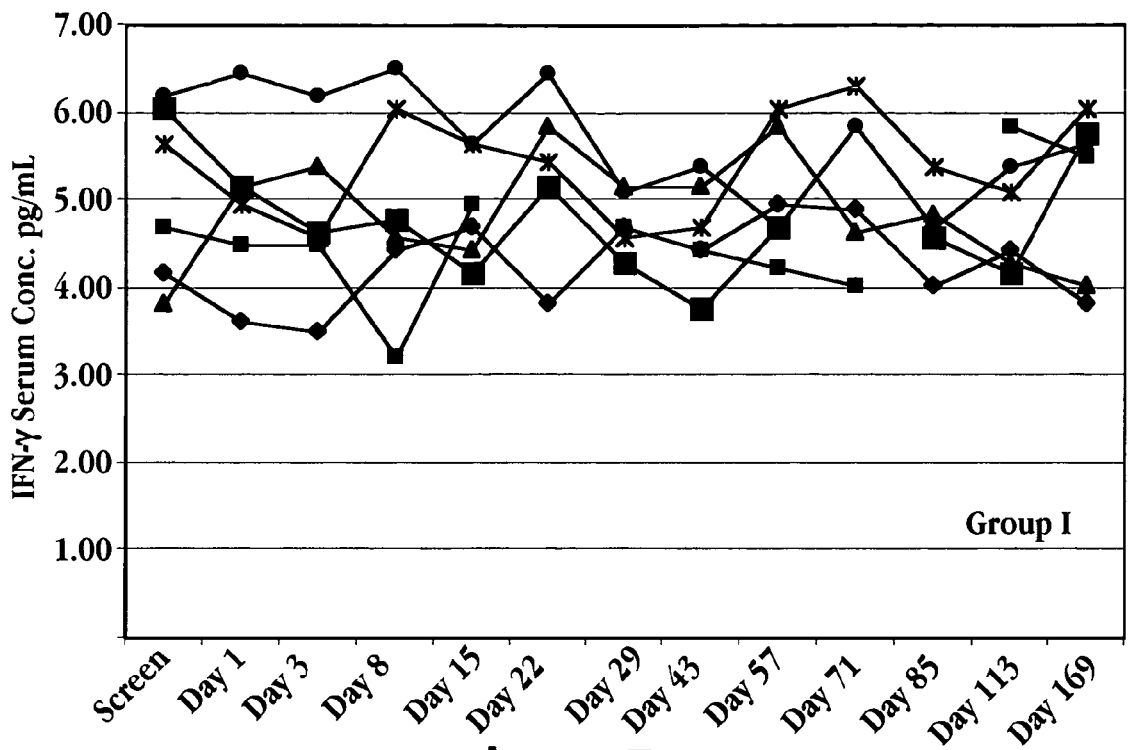
FIGS. 5A–5C are graphs showing the IFN-γ serum level, in pg/mL, in human patients suffering from hepatitis C and treated orally with IFNτ, as a function of time, in days, for the six patients in Test Group I treated daily with 0.33 mg IFNτ three times daily (FIG. 5A), for the six patients in Test Group II treated daily with 1.0 mg IFNτ three times daily (FIG. 5B); and for the six patients in Test Group IIII treated daily with 3 mg IFNτ three times daily (FIG. 5C).
Figure 5B:
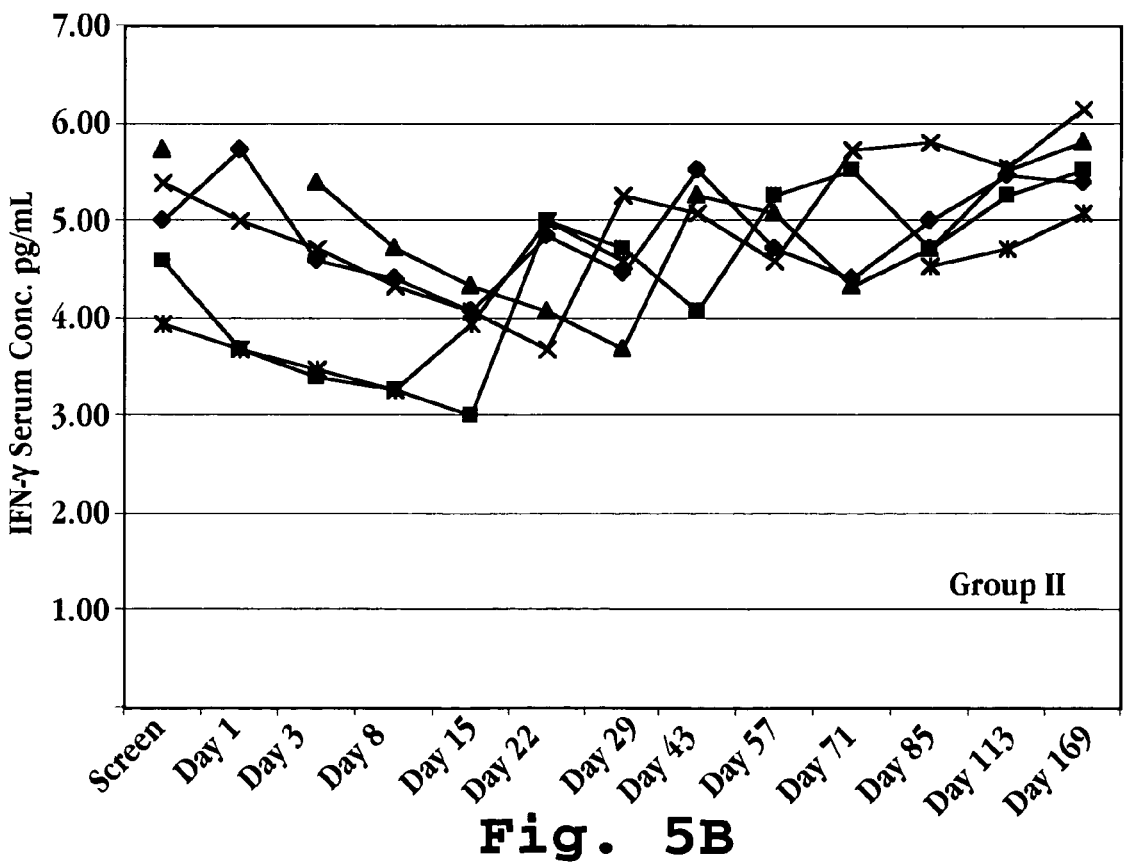
Figure 5C:
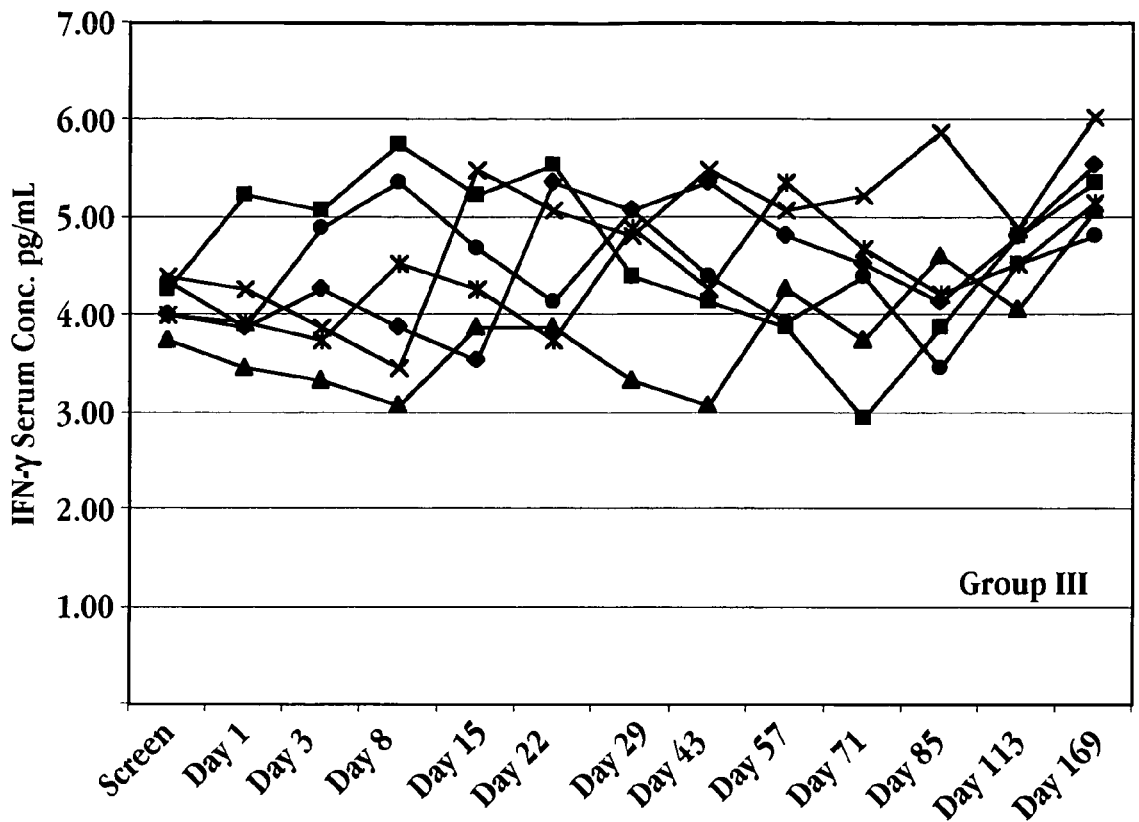

FIGS. 5A–5C are graphs showing the IFN-γ serum level, in pg/mL, for the hepatitis C patients in this study. FIG. 5A shows the IFN-γ levels for the six patients in Test Group I treated daily with 0.33 mg IFNτ three times daily. An overall trend of maintaining IFN-γ levels at the baseline level and toward slightly decreasing IFN-γ levels is apparent.

FIG. 5B shows the IFN-γ serum levels for the six patients in Test Group II treated daily with 1.0 mg IFNτ three times daily. A decrease in IFN-γ levels at the early phase of treatment, from about days 3 to 15 is apparent. The levels then returned to baseline and were maintained at about pre-dosing levels for the remainder of the test period.

FIG. 5C shows the IFN-γ serum levels for the six patients in Test Group IIII treated daily with 3 mg IFNτ three times daily. While some patients experienced a defined decrease in the IFN-γ level, overall the treatment group appeared to have little change in the level over the treatment period. An increase in the IFN-γ levels upon cessation of dosing is seen, from days 85–169. This suggests that a reduction in levels to some degree was achieved by administration of IFNτ.

Figure 5D:
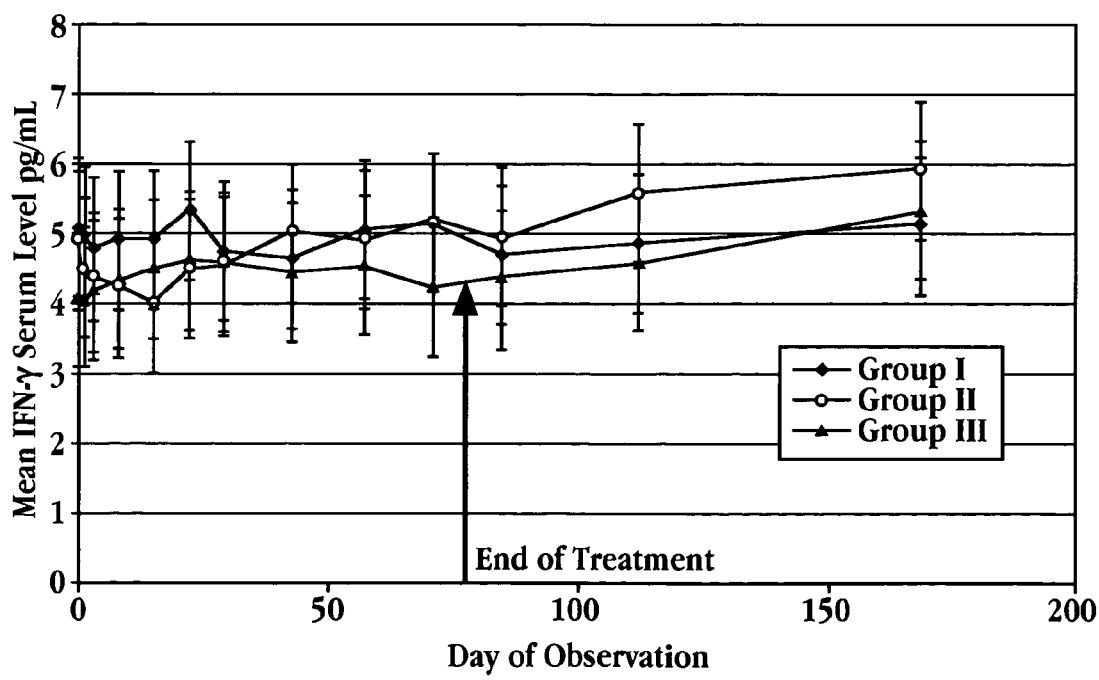
FIG. 5D is a summary plot for the test Groups I, II, and III in FIGS. 5A–5C, showing the mean serum IFN-γ levels as a function of time for test Group I (diamonds, 0.33 mg three times daily), Group II (circles, 1 mg three times daily), and Group III (triangles, 3 mg three times daily).

FIG. 5D is a summary plot for the test Groups I, II, and III in FIGS. 5A–5C, showing the mean serum IFN-γ levels as a function of time for test Group I (diamonds, 0.33 mg three times daily), Group II (circles, 1 mg three times daily), and Group III (triangles, 3 mg three times daily) as a function of time. It is clear that administration of IFNτ either (1) caused no significant change in IFN-γ levels, with the level remaining essentially at the screen, pre-dosing level, or (2) caused a reduction in IFN-γ level from the baseline, pre-dosing level.

Thus, the invention contemplates, in another aspect, a method of reducing the blood level of IFN-γ in a subject by administering IFNτ to the subject in an amount effective to decrease the subject's IFN-γ blood level relative to the IFN-γ blood level in the absence of IFNτ administration. This method finds use particularly for patients taking an agent that causes an elevated IFN-γ level or for patients suffering from a condition that elevates their IFN-γ levels. Thus, the invention also contemplates a method of preventing an increase in the blood level of IFN-γ in a subject at risk of an elevated IFN-γ blood level due to (i) administration of a therapeutic agent or (ii) a disease condition, by administering IFNτ to the subject in an amount effective to decrease the subject's IFN-γ blood level relative to the IFN-γ blood level in the absence of IFNτ administration. As noted above, treatment of multiple sclerosis with IFNβ causes an increase level of IFNγ in patients. Co-administration (simultaneous or sequential administration) of IFNτ will assist in maintaining the IFNγ level at the level prior to treatment. Typically, the amount of IFNτ sufficient to produce such a decrease in subject's IFN-γ blood level is greater than about $5 \times 10^8$ U/day, more preferably $0.5 \times 10^9$ U/day or more, still more preferably $1 \times 10^9$ U/day or more.

FIGS. 6A–6F show IL-10 (diamonds) and IFN-γ (squares) serum concentrations, both in pg/mL, for selected individual hepatitis C patients from the treatment Groups I, II, and III discussed with respect to FIGS. 4–5.

Figure 6A:
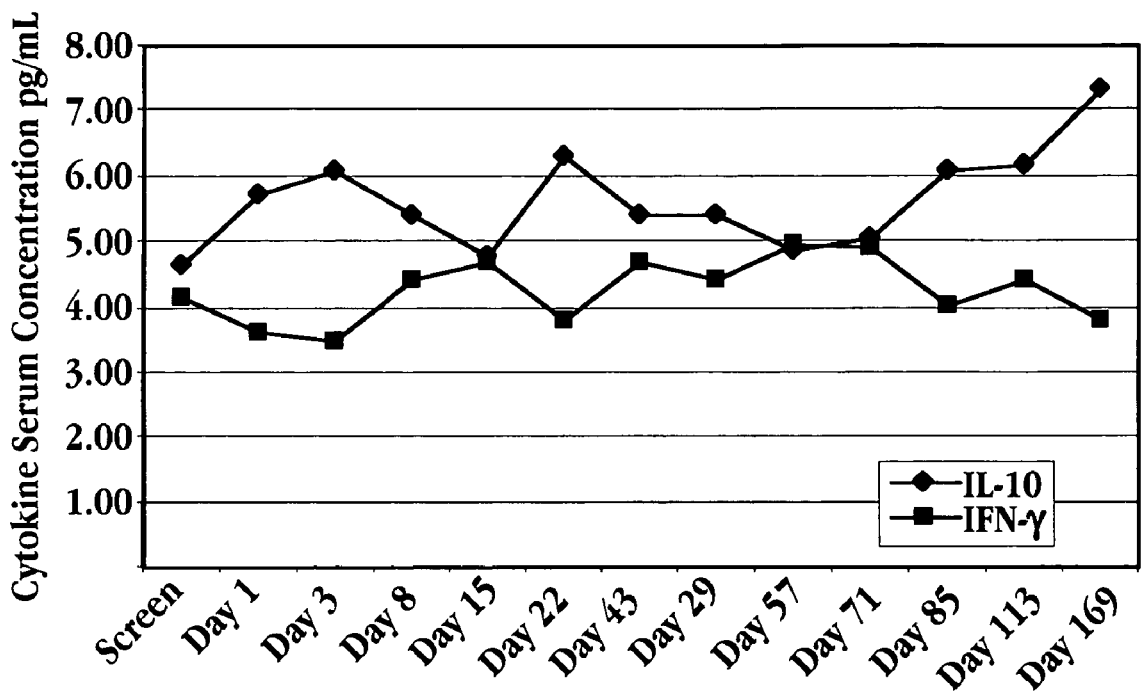
FIGS. 6A–6F show IL-10 (diamonds) and IFN-γ (squares) serum concentrations, both in pg/mL, for selected individual patients from the treatment Groups I, II, and III discussed with respect to FIGS. 4–5.

FIG. 6A shows the IL-10 (diamonds) and IFN-γ (squares) serum concentrations for patient no. 101 in test group I, treated with 0.33 mg IFNτ three times daily, for a daily dose of 1 mg IFNτ. The baseline levels of IL-10 and IFN-γ were on average 5.2 pg/mL and 3.9 pg/mL, respectively (averages of values at Screen and at Day 1), to give an initial IL-10/IFN-γ ratio of 1.3. During treatment with IFNτ, the IL-10/IFN-γ ratio increased to 1.6 at Day 22, with a return to the baseline ratio thereafter, until cessation of dosing at Day 84.

Figure 6B:
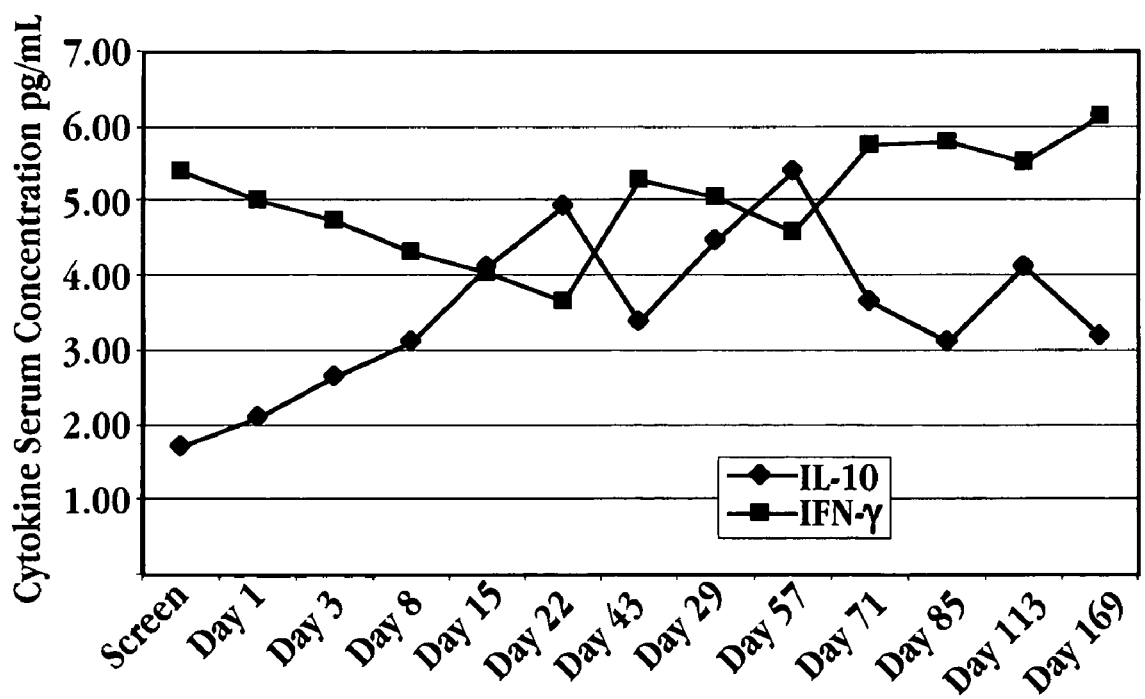

FIG. 6B shows the IL-10 (diamonds) and IFN-γ (squares) serum concentrations for patient no. 205 in test Group II, treated with 1.0 mg IFNτ three times daily, for a daily dose of 3 mg IFNτ. The baseline levels of IL-10 and IFN-γ were on average 3.8 pg/mL and 5.2 pg/mL, respectively (averages of values at Screen and at Day 1), to give an initial IL-10/IFN-γ ratio of 0.73. During treatment with IFNτ, the IL-10/IFN-γ ratio approached and reached 1 at Day 15. Thus, treatment with IFNτ resulted in modulation of the IL-10/IFN-γ ratio by increasing the ratio about 25%.

Figure 6C:
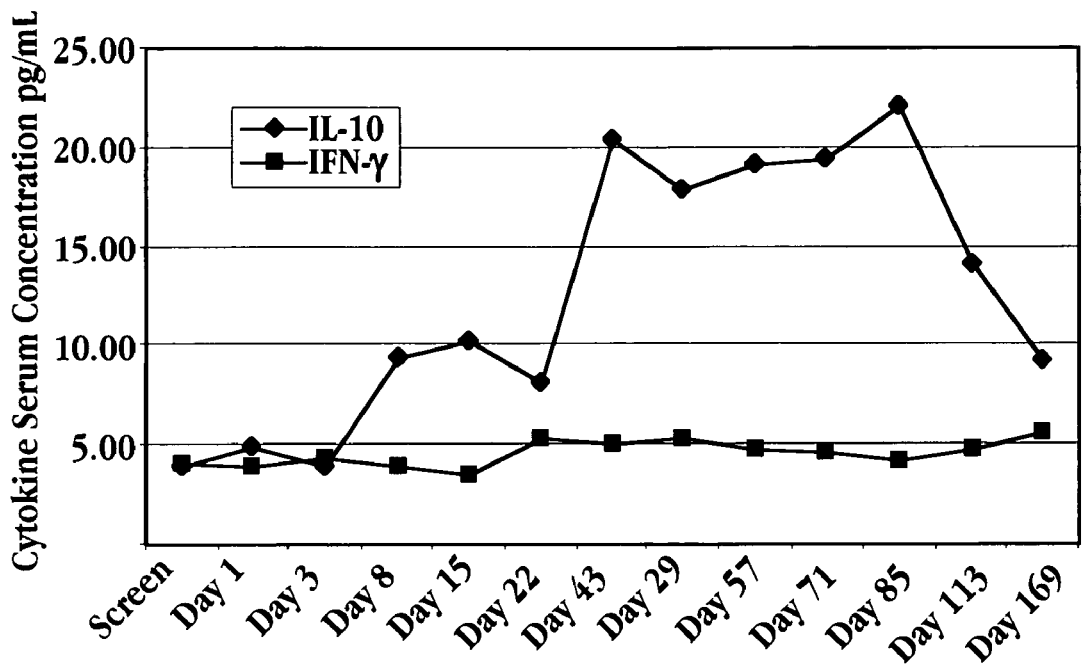

FIG. 6C shows the IL-10 (diamonds) and IFN-γ (squares) serum concentrations for patient no. 301 in test Group III, treated with 3.0 mg IFNτ three times daily, for a daily dose of 9 mg ($9 \times 10^8$ U) IFNτ. The baseline levels of IL-10 and IFN-γ were on average 4.4 pg/mL and 3.9 pg/mL, respectively (averages of values at Screen and at Day 1), to give an initial IL-10/IFN-γ ratio of about 1.0. During treatment with IFNτ, the IL-10 level increased 4–5 fold, a substantial increase, while the IFN-γ level was maintained at around the initial level of 4–5 pg/mL. Thus, the IL-10/IFN-γ ratio increased upon dosing with IFNτ from about 1.0 to around 4.0, a four-fold increase.

Figure 6D:
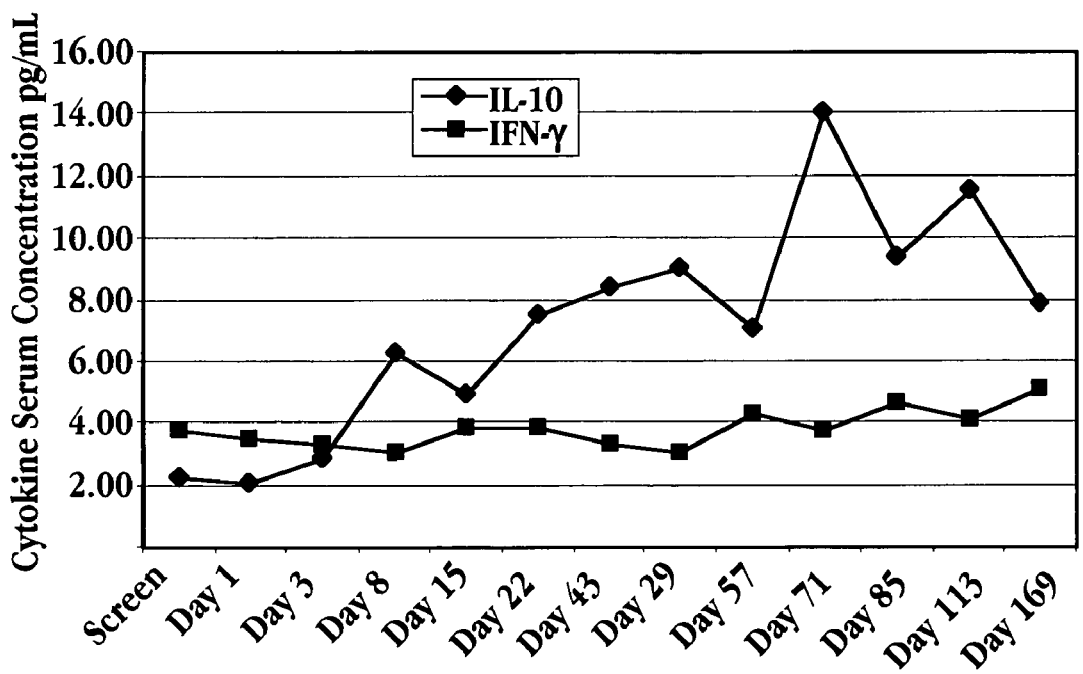
Figure 6E:
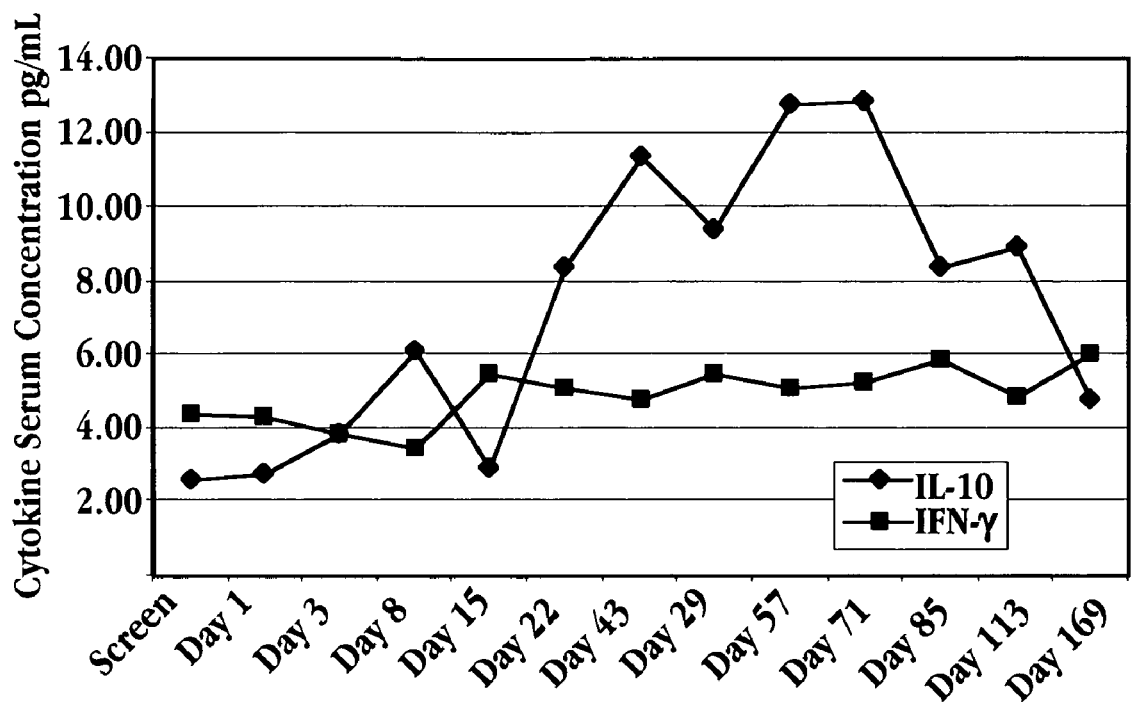
Figure 6F:
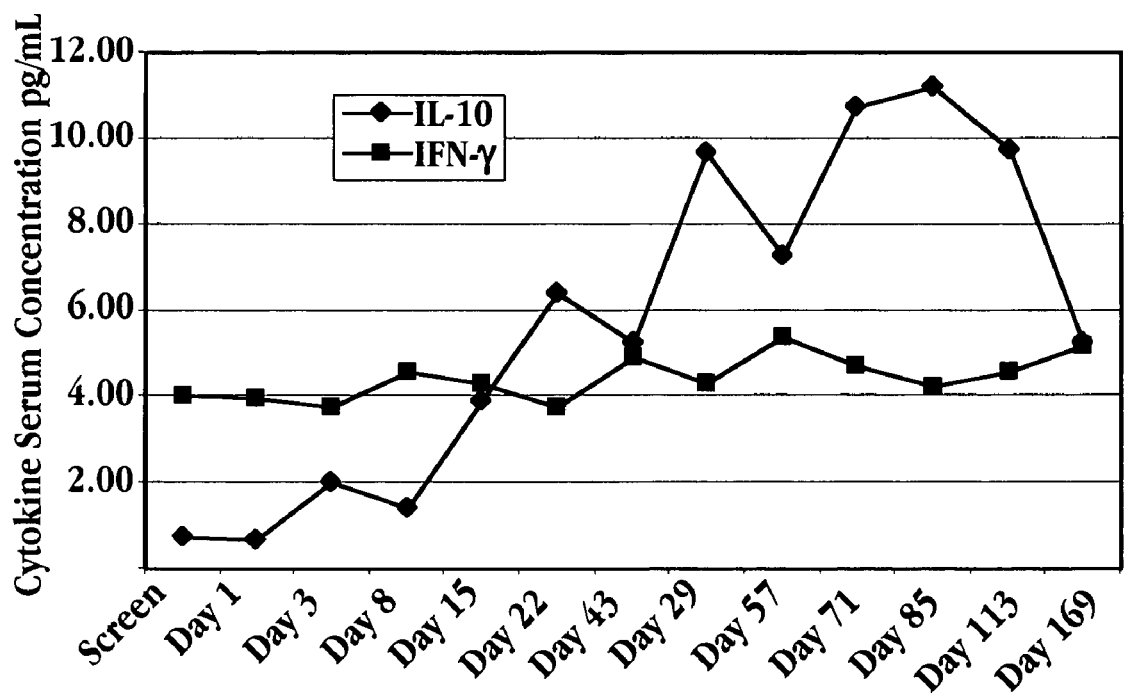

FIGS. 6D–6F show the IL-10 (diamonds) and IFN-γ (squares) serum concentrations for patient nos. 303, 304, and 305 in test Group III, treated with 3.0 mg IFNτ three times daily, for a daily dose of 9 mg IFNτ. An analysis of the IL-10/IFN-γ ratios is similar to that for patient no. 301, discussed in FIG. 6C. Specifically, FIG. 6D shows the data for patient no. 303. In this patient, the IL-10 blood concentration increased by about four-fold from baseline level by test Day 43 and increased by more than six-fold by test Day 71. The IFN-γ blood level remained substantially constant. Thus, the IL-10/IFN-γ blood ratio increased from a baseline value of 0.6 to greater than 3, a five-fold increase (500% increase).

FIG. 6E shows the data for patient no. 304 in Group III. The patient's IL-10 blood level increased 4–5 fold during treatment with IFNτ, whereas the IFNγ level remained essentially unchanged. Thus, the IL-10/IFNγ ratio increased from its initial value of 0.6 to 2.6 at Day 71, an increase of more than 400%.

FIG. 6F shows the data for patient no. 305 in Group III. The increasing IL-10 blood level during the treatment period is evident, with an increase from 0.7 pg/mL to more than 9 pg/mL by Day 43. The IFNγ level remained essentially unchanged, resulting in an IL-10/IFNγ ratio increase of more than 10 fold.

In summary, the data presented for the patients in Group III show that administration of IFNτ was effective to increase the IL-10/IFN-γ ratio. In particular, the IL-10 blood levels were measurably increased by oral administration of IFNτ, as evidenced by the statistical increase in IL-10 blood concentrations. The IL-10 blood levels were increased by more than 25%, and in this patient population, the increase in IL-10 blood concentrations was considerably greater.

In another study, five patients suffering from hepatitis C were recruited for treatment with IFNτ. In this study, described in Example 3, the patients were treated with 7.5 mg IFNτ twice daily, for a daily dose of 15 mg IFNτ ($1.5 \times 10^9$ antiviral units). The first dose was taken in the morning, before breakfast, and the second dose was taken at least three hours after an evening meal. Blood samples were taken at defined intervals over a 113 day test period; dosing of IFNτ was terminated at test Day 84. The samples were analyzed for IL-10, IL-12, and IFN-γ levels in the serum using commercially available methods.

Figure 7A:
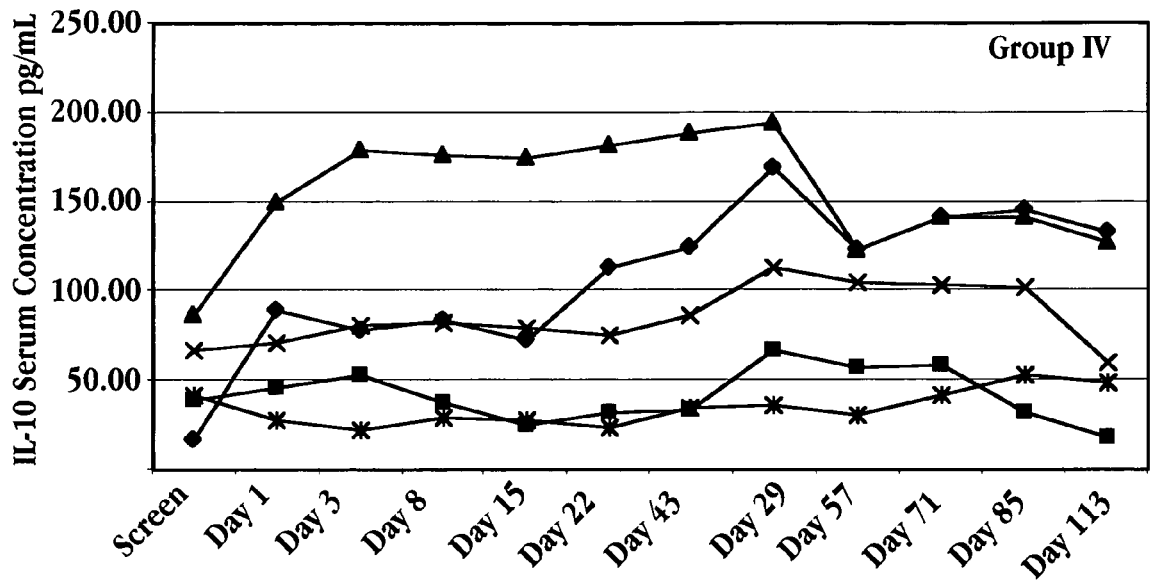
FIGS. 7A–7B are graphs showing the IL-10 serum level (FIG. 7A) and the IFN-γ serum level (FIG. 7B), in pg/mL, in human patients suffering from hepatitis C and treated orally with IFNτ, as a function of time, in days, where a 7.5 mg dose of IFNτ was given twice a day on an empty stomach.
Figure 7B:
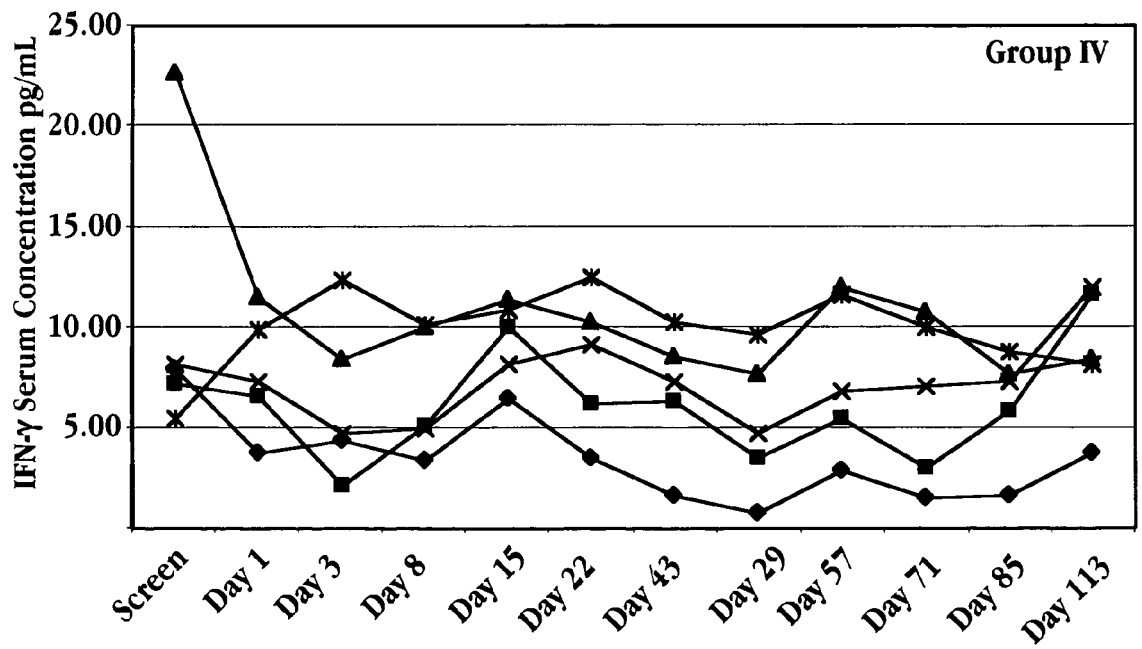

FIGS. 7A–7B are graphs showing the IL-10 serum level (FIG. 7A) and the IFN-γ serum level (FIG. 7B), in pg/mL, in the five patients, as a function of time, in days. As seen in FIG. 7A, three of the patients (patients represented by triangles, diamonds, and x's) shows an increased IL-10 level over the period of IFNτ dosing, from Day 1 to Day 84. FIG. 7B shows that all five patients had a reduction in IFNγ blood levels over the dosing period from Day 1 to Day 84. At the end of dosing, the IFN-γ levels increase, as seen during the period from Day 85 to Day 113.

The blood samples drawn from the patients in this study were also analyzed for IL-12 levels. IL-12 is a pro-inflammatory cytokine and contributes to the pathogenesis of multiple sclerosis. The literature reports that (1) increased production of IL-12 is a key mechanism in the pathogenesis of multiple sclerosis (Filson et al., *Clin. Immunol.*, 106(2): 127 (2003); (2) MS patients typically display decreased IL-10 and increased IL-12 levels, and the levels of these cytokines correlate with the disease stage (van Boxel-Dezaire et al., *Ann. Neurol.*, 45:695 (1999)). With respect to viral infections, a high IL-12 level has also been shown to exacerbate bacterial colonization of *B. pertussis* (Carter et al., *Clin. Exp. Immunol.*, 135(2):233 (2004)). Thus, it was desirable to monitor the IL-12 levels in the HCV patients enrolled in this study.

FIGS. 8A–8D show the IL-10 (diamonds), IFN-γ (squares), and IL-12 (triangles) serum levels, in pg/mL, for the six patients in this study (Example 3). The actual IL-12 concentrations are 10 times the value shown in FIGS. 8A–8D (actual values were divided by 10 to show all data on a single graph).

Figure 8A:
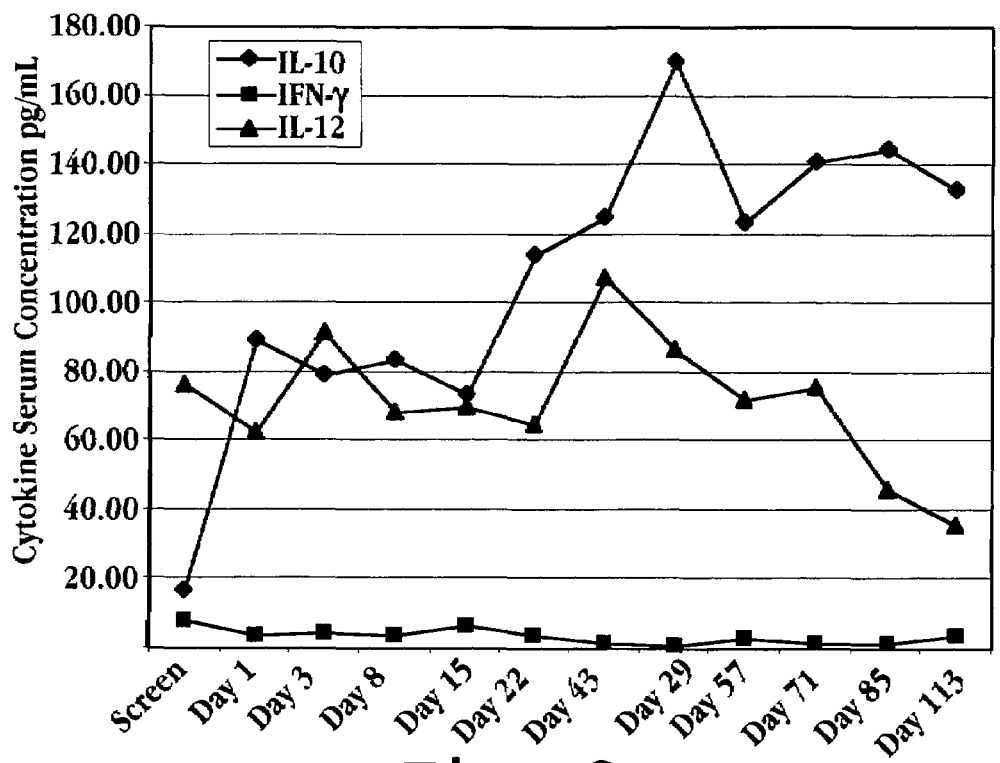
FIGS. 8A–8D show the IL-10 (diamonds), IFN-γ (squares), and IL-12 (triangles) serum levels, in pg/mL, for the patients treated as described with respect to FIGS. 7A–7B.

FIG. 8A shows the data for patient no. 401. As seen, the IL-10 level increased over the treatment period when IFNτ was administered, IFN-γ was unchanged or decreased slightly, and IL-12 fluctuated initially and then was down-regulated after about Day 29. The initial IL-10 level was 53.1 pg/mL and the initial, baseline IL-12 was 696 pg/mL, for an IL-10/IL-12 ratio of 0.08. During the treatment period, this ratio increased to between about 0.12–0.18, a 570–1200% increase. The IL-10 level in this patient increased from a baseline value of 53.1 pg/mL to greater than 140 pg/mL, an increase of more than 160% (2.6 fold).

Figure 8B:
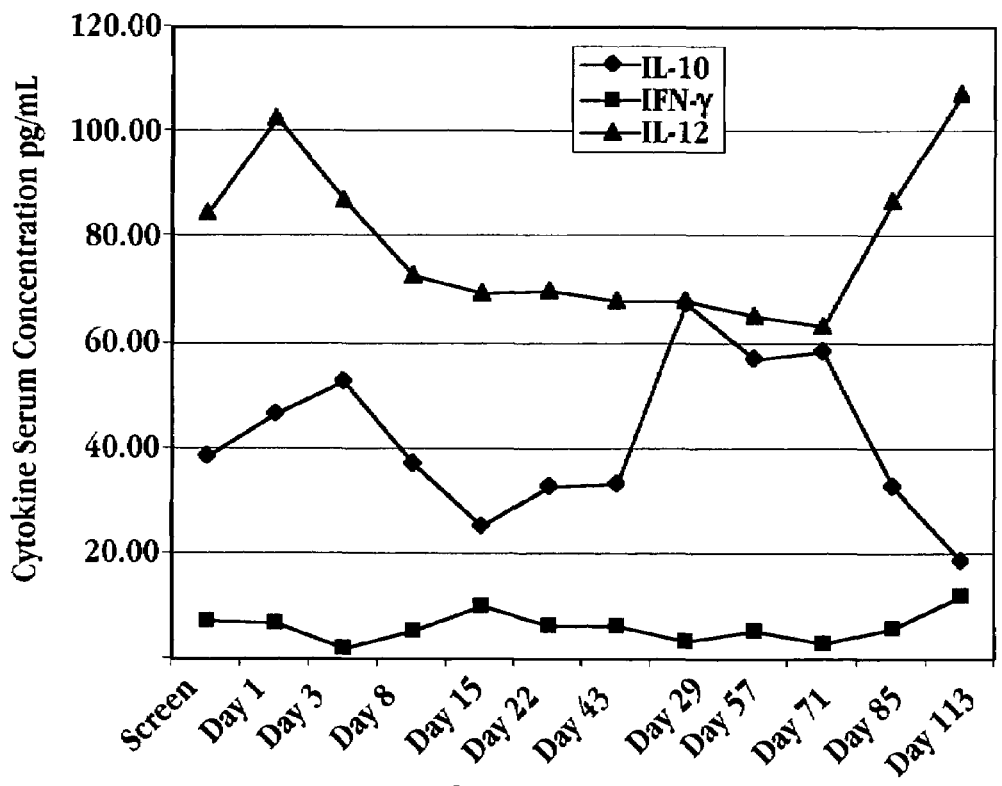
Figure 8C:
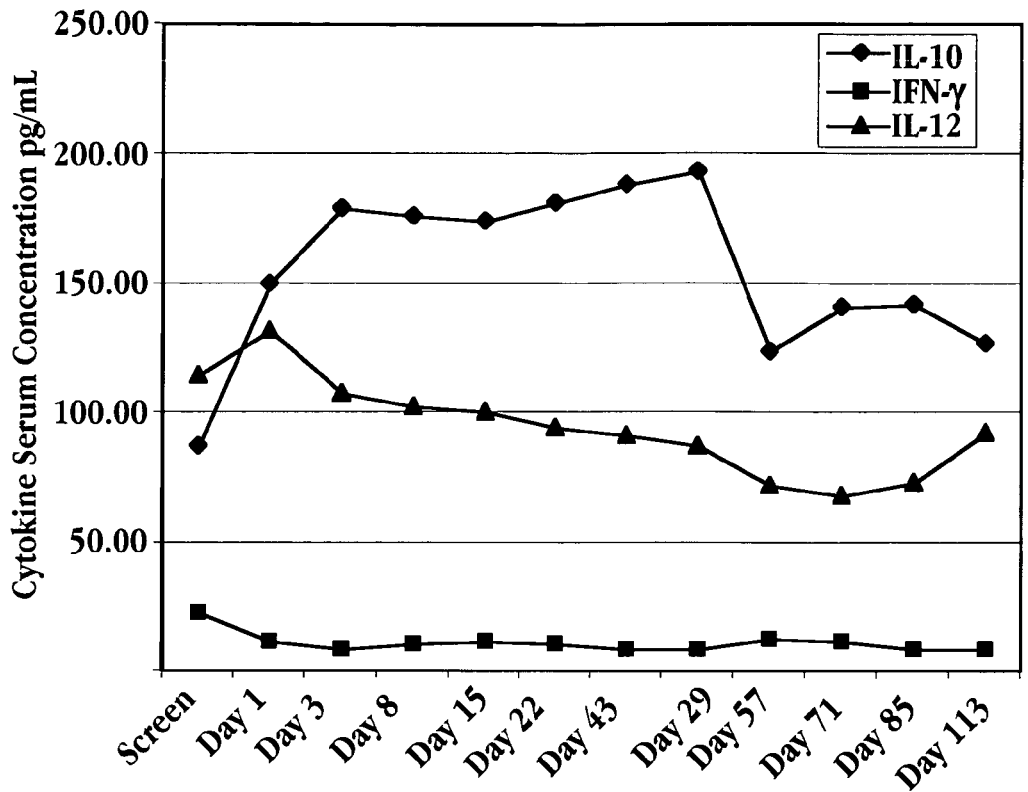

FIG. 8B shows the data for patient no. 402 and FIG. 8C shows the data for patient no. 403. Patient No. 402 had an initial, baseline IL-10 blood level of 42.7 pg/mL (average blood concentrations of Screen and Day 1). The IL-10 blood level peaked at Day 43, when the concentration reached 67 pg/mL, a 56% increase. The IFNγ blood concentration fluctuated around the baseline level. The IL-12 blood level prior to treatment was 934 pg/mL, for an initial IL-10/IL-12 ratio of 0.046. At Day 43, the IL-10/IL-12 ratio was 0.088, a 90% increase from the baseline ratio.

In FIG. 8C the patient's initial IL-10/IL-12 ratio was 0.10 (IL-10=118.5 pg/mL; IL-12=1227 pg/mL). This ratio increased over the treatment period, with a ratio value of 0.22 at Day 43, a 2.2 fold increase in IL-10/IL-12 ratio. The patient's IL-10 blood level peaked on Day 43 at a value 63% higher than the baseline level.

Figure 8D:
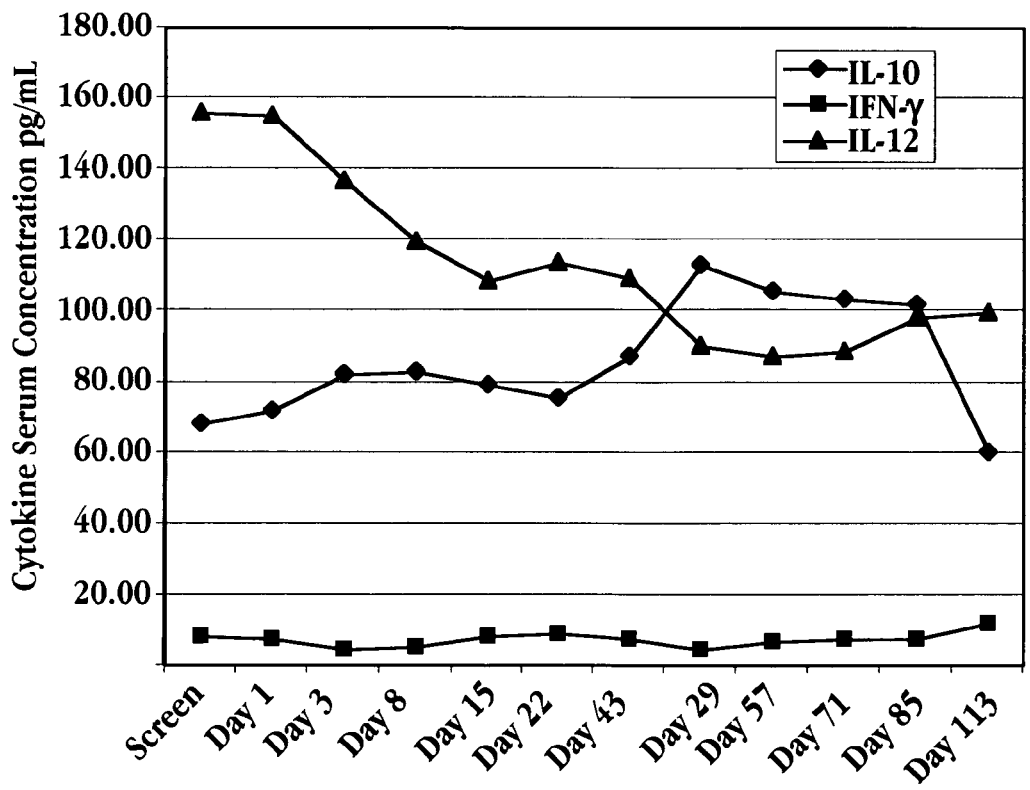

FIG. 8D shows the data for patient no. 404. This patient had an initial IL-10 blood level of 69.6 pg/mL and an initial IL-12 level of 1552 pg/mL for an initial IL-10/IL-12 ratio of 0.045. During treatment with IFNτ at a dosage of $1.5 \times 10^9$ U per day the IL-10 blood level rose to 113 pg/mL on Day 43, an approximately 60% increase. The IL-12 at Day 43 had decreased to 900 pg/mL, providing an Il-10/IL-12 ratio at Day 43 of 0.12.

Patient No. 405 in this study had an initial IL-10 blood concentration of 34.9 pg/mL and an initial IL-12 blood concentration of 976 pg/mL (IL-10/IL-12 ratio 0.036; data not shown). Administration of IFNτ at a dosage of $1.5 \times 10^9$ U per day was effective to increase the IL-10/IL-12 ratio to 0.058 at Day 71 of the treatment period, a 60% increase. The IL-10 blood concentration increased 20% from the initial pre-treatment level to the level at Day 71.

Accordingly, the invention contemplates a method of increasing the IL-10/IL-12 blood ratio in subjects suffering from an autoimmune disorder by administering interferon-tau to the subject in an amount effective to produce an initial measurable increase in the subject's blood IL-10 level, relative to the blood IL-10 level in the subject in the absence of interferon-tau administration, and a decrease in the subject's IL-12 blood level, relative to the IL-12 level in the absence of interferon-tau administration. The invention also contemplates a method of inhibiting progression of an autoimmune condition in a subject, by administering interferon-tau to the subject in an amount effective to produce an initial measurable increase in the subject's blood IL-10 level, relative to the blood IL-10 level in the subject in the absence of interferon-tau administration, and a decrease in the subject's IL-12 blood level, relative to the IL-12 level in the absence of interferon-tau administration. In particular, the patients treated with greater than about $5 \times 10^8$ U of IFNτ had increased IL-10 blood levels of more than 25%, and in many cases of more than 50%. In the same patients, the IFNγ blood concentrations were essentially unchanged or were decreased and the IL-12 levels generally decreased.

In summary, the invention contemplates administration of IFNτ orally to a patient in need of treatment, where the initial dose(s) of IFNτ is selected to achieve an increased blood IL-10 level for that particular patient, and/or a decreased or unchanged IFN-γ level, and/or a decreased IL-12 level. The IFNτ is preferably administered in a form that targets the intestinal tract of the patient, rather than the oral cavity. Dosage selection can be made or confirmed, for example, by monitoring blood IL-10 levels e.g., prior to treatment and following initiation of treatment. Alternatively, an effective dose may be predetermined from model patient responses to given doses under different disease conditions. For example, a patient within a given age range and having a specified condition, e.g., a viral infection or an autoimmune condition, may be monitored for changes in blood IL-10 in response to different initial IFNτ levels, to predetermine suitable doses for patients with that age/disease profile, and such dosing guidelines may be supplied to the treating physician. One aspect of the present invention includes an IFNτ therapy kit that includes IFNτ in an oral delivery form suitable for targeting the protein to the intestinal tract, e.g., an enteric coated form of IFN-tau, and product literature or insert that provides guidelines for effective doses, under different patient condition; that is, doses effective to produce a measurable increase in IL-10 blood levels. Preferably, the insert provides a range of doses and predicted initial changes in IL-10 response.

Following the initial administration, or when a dose is reached that produces a measurable increase in blood IL-10 levels (an effective dose), the administration of an effective dose IFNτ is continued, preferably on a daily or several-time-weekly basis, for an extended treatment period. The effective dose that is administered on an extended basis is one effective to produce an initial measurable increase in blood IL-10, independent of the behavior of actual blood IL-10 levels over the extended treatment period, whether or not the continuing effective dose is the same or different from the initial effective dose. Thus, during the treatment period, blood IL-10 levels may remain constant at an elevated level, continue to increase, or even decrease (for example, in response to decreasing levels of infecting virus), even though the patient is continuing to receive an IFNτ dose effective to produce an initial measurable increase in blood IL-10 levels. This effective dose is typically in the range of greater than about $5 \times 10^8$ Units per day and up to about $10^{12}$ Units per day; more specifically, the dose is greater than about $5 \times 10^8$ Units per day, more preferably about $0.5 \times 10^9$ Units or more per day, still more preferably about $1 \times 10^9$ Units or more per day. The dose can be adjusted to achieve a desired initial increase in blood IL-10, e.g., between 1.5 and 4 fold normal, untreated levels.

It will be appreciated that for some patients and for some conditions, administration of IFNτ in combination with another therapeutic agent is contemplated. For example, combination of IFNτ with other recognized hepatitis antiviral agents may be beneficial in some patients. Similarly, combination of IFNτ with agents used to treat autoimmune conditions will be beneficial in treating the condition. Combination of IFNτ with chemotherapeutic agents in patients suffering from cellular proliferation is also contemplated. More generally, combination of IFNτ with any known pharmaceutical agent is contemplated and exemplary agents are given below. It will be appreciated that "combination" of IFNτ with a second agent intends sequential or simultaneous administration of the two agents, where the sequential administration can be immediate or non-immediate.

III. Methods of Use

In a first aspect, the invention provides a method for treating in a human subject a disease or condition responsive to interferon therapy. A condition "responsive to interferon therapy" is one in which the existence, progression, or symptoms of the condition is altered upon administration of an interferon, in particular a type-I interferon, and more particularly, interferon-tau. Conditions responsive to treatment with IFNα or IFNβ may also respond to treatment with IFNτ. More preferably, a condition responsive to interferon therapy is one where the existence, progression, or symptoms of the condition are alleviated by IFNτ administered in a non-oral route, such as injection. The method described herein encompasses providing IFNτ, preferably in an orally-administrable dosage form for administration to the stomach and/or intestines, in an amount effective for therapy, as evidenced by an increase in blood IL-10 level determined from studies on similarly situated patients or on the particular individual patient being treated. The dose of IFNτ sufficient to increase blood IL-10 level can also be effective to cause a reduction in IL-12 blood level, with a reduction or no change in IFN-γ level.

IFN has biological activity as an antiviral agent, an anti-proliferative agent, and in treatment of autoimmune disorders (see for example U.S. Pat. Nos. 5,958,402; 5,942,223; 6,060,450; 6,372,206, which are incorporated by reference herein). Accordingly, the invention contemplates oral administration of IFNτ for treatment of any condition responsive to IFNτ when administered via injection. Conditions and diseases which may be treated using methods of the present invention include autoimmune, inflammatory, viral infections, proliferative and hyperproliferative diseases, as well as immunologically-mediated diseases.

A. Treatment of Immune System Disorders

The method of the present invention is advantageous for treating conditions relating to immune system hypersensitivity. There are four types of immune system hypersensitivity (Clayman, C. B., Ed., *AMERICAN MEDICAL ASSOCIATION ENCYCLOPEDIA OF MEDICINE*, Random House, New York, N.Y., (1991)). Type I, or immediate/anaphylactic hypersensitivity, is due to mast cell degranulation in response to an allergen (e.g., pollen), and includes asthma, allergic rhinitis (hay fever), urticaria (hives), anaphylactic shock, and other illnesses of an allergic nature. Type II, or autoimmune hypersensitivity, is due to antibodies that are directed against perceived "antigens" on the body's own cells. Type III hypersensitivity is due to the formation of antigen/antibody immune complexes which lodge in various tissues and activate further immune responses, and is responsible for conditions such as serum sickness, allergic alveolitis, and the large swellings that sometimes form after booster vaccinations. Type IV hypersensitivity is due to the release of lymphokines from sensitized T-cells, which results in an inflammatory reaction. Examples include contact dermatitis, the rash of measles, and "allergic" reactions to certain drugs.

The mechanisms by which certain conditions may result in hypersensitivity in some individuals are generally not well understood, but may involve both genetic and extrinsic factors. For example, bacteria, viruses or drugs may play a role in triggering an autoimmune response in an individual who already has a genetic predisposition to the autoimmune disorder. It has been suggested that the incidence of some types of hypersensitivity may be correlated with others. For example, it has been proposed that individuals with certain common allergies are more susceptible to autoimmune disorders.

Autoimmune disorders may be loosely grouped into those primarily restricted to specific organs or tissues and those that affect the entire body. Examples of organ-specific disorders (with the organ affected) include multiple sclerosis (myelin coating on nerve processes), type I diabetes mellitus (pancreas), Hashimotos thyroiditis (thyroid gland), pernicious anemia (stomach), Addison's disease (adrenal glands), myasthenia gravis (acetylcholine receptors at neuromuscular junction), rheumatoid arthritis (joint lining), uveitis (eye), psoriasis (skin), Guillain-Barré Syndrome (nerve cells) and Grave's disease (thyroid). Systemic autoimmune diseases include systemic lupus erythematosus and dermatomyositis. Another autoimmune disorder is Sjogren's syndrome, where white blood cells attack the moisture-producing glands. The hallmark symptoms of Sjogren's syndrome are dry eyes and dry mouth, but it is a systemic disease, affecting many organs.

Other examples of hypersensitivity disorders include asthma, eczema,. atopical dermatitis, contact dermatitis, other eczematous dermatitides, seborrheic dermatitis, rhinitis, Lichen planus, Pemplugus, bullous Pemphigoid, Epidermolysis bullosa, uritcaris, angioedemas, vasculitides, erythemas, cutaneous eosinophilias, Alopecia areata, atherosclerosis, primary biliary cirrhosis and nephrotic syndrome. Related diseases include intestinal inflammations, such as Coeliac disease, proctitis, eosinophilia gastroenteritis, mastocytosis, inflammatory bowel disease, Crohn's disease and ulcerative colitis, as well as food-related allergies. Ankylosing spondylitis is another example of an autoimmune, inflammatory disease, where some or all of the joints and bones of the spine fuse together.

Autoimmune diseases particularly amenable for treatment using the methods of the present invention include multiple sclerosis, type I (insulin dependent) diabetes mellitus, lupus erythematosus, amyotrophic lateral sclerosis, Crohn's disease, rheumatoid arthritis, stomatitis, asthma, uveitis, allergies, psoriasis, Ankylosing spondylitis, Myasthenia Gravis, Grave's disease, Hashimoto's thyroiditis, Sjogren's syndrome, and inflammatory bowel disease.

The method of the present invention is used to therapeutically treat and thereby alleviate autoimmune disorders, such as those discussed above. Treatment of an autoimmune disorder is exemplified herein with respect to the treatment of EAE, an animal model for multiple sclerosis. When used to treat an autoimmune disorder, IFNτ is administered at a dose sufficient to achieve the measurable increase in IL-10 during the initial phase(s) of IFNτ administration. Once a desired effective dose is achieved, the patient is treated over an extended period with an effective IFNτ dose, independent of further changes in IL-10 blood levels. The treatment period extends at least over the period of time when the patient is symptomatic. Upon cessation of symptoms associated with the autoimmune condition, the dosage may be adjusted downward or treatment may cease. The patient may be co-treated during the treatment period of IFNτ treatment with another agent, such as a known anti-inflammatory or immune-suppressive agent.

Also contemplated is a method of preventing progression of an autoimmune condition, by administering IFNτ in a dose that elevates the IL-10 level in a subject. Also contemplated is a method of inhibiting onset of an autoimmune condition, by administering IFNτ in a dose effective to increase IL-10 serum levels, preferably with no change or a reduction in the IFN-γ level. Also contemplated is a method of treating an autoimmune condition by administering IFNτ in a dose effective to increase the IL-10/IL-12 serum ratio. As discussed above, the dose of IFNτ is provided in an oral form and is typically greater than about $5 \times 10^8$ Units/day.

B. Treatment of Viral Infections

The method of the invention is also used to treat conditions associated with viral infection. The antiviral activity of IFNτ has broad therapeutic applications without the toxic effects that are usually associated with IFNαs, and IFNτ exerts its therapeutic activity without adverse effects on the cells. The relative lack of cytotoxicity of IFNτ makes it extremely valuable as an in vivo therapeutic agent and sets IFNτ apart from most other known antiviral agents and all other known interferons.

Formulations containing IFNτ can be orally-administered to inhibit viral replication. For use in treating a viral infection, the protein is administered at a dose sufficient to achieve a measurable increase in blood IL-10 in the patient. Thereafter, treatment is continued at an effective dose, independent of further changes in blood IL-10 levels, for example, a fall in IL-10 blood levels due to reduction in viral load. Administration of IFNτ is continued until the level of viral infection, as measured for example from a blood viral titer or from clinical observations of symptoms associated with the viral infection, abates.

The viral infection can be due to a RNA virus or a DNA virus. Examples of specific viral diseases which may be treated by orally-administered IFNτ include, but are not limited to, hepatitis A, hepatitis B, hepatitis C, non-A, non-B, non-C hepatitis, Epstein-Barr viral infection, HIV infection, herpes virus (EB, CML, herpes simplex), papilloma, poxvirus, picorna virus, adeno virus, rhino virus, HTLV I, HTLV II, and human rotavirus. The patient may be co-treated during the IFNτ treatment period with a second antiviral agent and exemplary agents are given below.

C. Method for Treating Conditions of Cellular Proliferation

In another embodiment, the methods of the invention are contemplated for treatment of conditions characterized by hyperproliferation. IFNτ exhibits potent anticellular proliferation activity. Accordingly, a method of inhibiting cellular growth by orally administering IFNτ is contemplated, in order to inhibit, prevent, or slow uncontrolled cell growth.

Examples of cell proliferation disorders in humans which may be treated by orally-administered IFNτ include, but are not limited to, lung large cell carcinoma, colon adenocarcinoma, skin cancer (basal cell carcinoma and malignant melanoma), renal adenocarcinoma, promyelocytic leukemia, T cell lymphoma, cutaneous T cell lymphoma, breast adenocarcinoma, steroid sensitive tumors, hairy cell leukemia, Kaposi's Sarcoma, chronic myelogenous leukemia, multiple myeloma, superficial bladder cancer, ovarian cancer, and glioma.

For use in treating a cell-proliferation condition, IFNτ is administered at a dose sufficient to achieve an initial measurable increase in blood IL-10 in the patient. Thereafter, treatment is continued at an effective dose, independent of further changes in blood IL-10 levels, for example, a fall in IL-10 blood levels due to a reduction in cancer cells in the body. Administration of IFNτ at an effective dose is continued until a desired level of regression is observed, as measured for example, by tumor size or extent of cancer cells in particular tissues.

The patient may be co-treated during the IFNτ treatment period with a second anticancer agent, e.g., cis-platin, doxorubicin, or taxol and the other agents given below.

D. Formulations and Dosages

Oral preparations containing IFNτ can be formulated according to known methods for preparing pharmaceutical compositions. In general, the IFNτ therapeutic compositions are formulated such that an effective amount of the IFNτ is combined with a suitable additive, carrier and/or excipient in order to facilitate effective oral administration of the composition. For example, tablets and capsules containing IFNτ may be prepared by combining IFNτ (e.g., lyophilized IFNτ protein) with additives such as pharmaceutically acceptable carriers (e.g., lactose, corn starch, microcrystalline cellulose, sucrose), binders (e.g., alpha-form starch, methylcellulose, carboxymethylcellulose, hydroxypropylcellulose, hydroxypropylmethylcellulose, polyvinylpyrrolidone), disintegrating agents (e.g., carboxymethylcellulose calcium, starch, low substituted hydroxy-propylcellulose), surfactants (e.g., Tween 80, polyoxyethylene-polyoxypropylene copolymer), antioxidants (e.g., L-cysteine, sodium sulfite, sodium ascorbate), lubricants (e.g., magnesium stearate, talc), or the like.

Further, IFNτ polypeptides of the present invention can be mixed with a solid, pulverulent or other carrier, for example lactose, saccharose, sorbitol, mannitol, starch, such as potato starch, corn starch, millopectine, cellulose derivative or gelatine, and may also include lubricants, such as magnesium or calcium stearate, or polyethylene glycol waxes compressed to the formation of tablets. By using several layers of the carrier or diluent, tablets operating with slow release can be prepared.

Liquid preparations for oral administration can be made in the form of elixirs, syrups or suspensions, for example solutions containing from about 0.1% to about 30% by weight of IFNτ, sugar and a mixture of ethanol, water, glycerol, propylene, glycol and possibly other additives of a conventional nature.

Another suitable formulation is a protective dosage form that protects the protein for survival in the stomach and intestines until absorbed by the intestinal mucosa. Protective dosage forms for proteins are known in the art, and include enteric coatings and/or mucoadhesive polymer coatings. Exemplary mucoadhesive polymer formulations include ethyl cellulose, hydroxypropylmethylcellulose, Eudragit®, carboxyvinly polymer, carbomer, and the like. A dosage form designed for administration to the stomach via ingestion for delivery of IFNτ in an active form to the intestinal tract, and particularly to the small intestine, is contemplated. Alternatively, IFNτ can be co-administered with protease inhibitors, stabilized with polymeric materials, or encapsulated in a lipid or polymer particle to offer some protection from the stomach and/or intestinal environment.

An orally-active IFNτ pharmaceutical composition is administered in a therapeutically-effective amount to an individual in need of treatment. The dose may vary considerably and is dependent on factors such as the seriousness of the disorder, the age and the weight of the patient, other medications that the patient may be taking and the like. This amount or dosage is typically determined by the attending physician. The dosage will typically be between about $6 \times 10^8$ and $5 \times 10^{12}$ Units/day, more preferably between $0.5 \times 10^9$ and $1 \times 10^{12}$ Units/day, still more preferably between about $1 \times 10^9$ and $1 \times 10^{12}$ Units/day. In one specific embodiment, IFN-τ is administered orally at a dosage of greater than about $5 \times 10^8$ Units/day, more preferably at a dosage of $0.5 \times 10^9$ Units/day or more, still more preferably at a dose of $1 \times 10^9$ Units/day or more.

Disorders requiring a steady elevated level of IFNτ in plasma will benefit from administration as often as about every two to four hours, while other disorders, such as multiple sclerosis, may be effectively treated by administering a therapeutically-effective dose at less frequent intervals, e.g., once a day or once every 48 hours. The rate of administration of individual doses is typically adjusted by an attending physician to enable administration of the lowest total dosage while alleviating the severity of the disease being treated. As discussed above, the method contemplates administering IFNτ orally at a first dose to a patient in need of treatment, and monitoring a biological marker to determine the individual patient response to the first dosage level. Monitoring can be readily done via a blood draw and analysis of a marker, such as IL-10 in the blood, using, for example, a ELISA or a radioimmunoassay kit. Accordingly, in another aspect, the invention contemplates a kit for using in treating a person suffering from a condition responsive to IFNτ. The kit includes a first part, comprised of a container containing one or more dosage form units designed for oral administration of IFNτ and a second part comprised of components required to monitor a biomarker of IFNτ, such as the components needed to analyze blood IL-10 levels.

Administration of IFNτ generally continues until a clinical endpoint is achieved. That clinical endpoint will vary according to the condition being treated, to the severity of the condition, and to the patient's individual characteristics (age, weight, health). Clinical endpoints are readily determined by an attending doctor or nurse and range from a temporary or permanent cessation of symptoms to resolution of the condition. For example, in patients suffering from an autoimmune condition, such as psoriasis, treatment with IFNτ may continue until the psoriasis has cleared. In multiple sclerosis patients, a suitable clinical endpoint would be a lessening of the severity of the symptoms. In persons afflicted with an viral infection, a suitable clinical endpoint would be a reduction in viral titer or an attenuation of the symptoms associated with the viral infection (fever, rash, malaise, etc.). In patients suffering from a condition characterized by cellular proliferation, a clinical endpoint at which to cease administration of IFNτ could be a regression in rate of cellular proliferation, as measured by regression of tumor size, or a slowing of cellular proliferation, as measured by a diminished rate of tumor growth.

Once the desired clinical endpoint is achieved, daily treatment with IFNτ can cease, however a maintenance dose can be administered if desired or as necessary. Subsequently, the dosage or the frequency of administration, or both, may be reduced, as a function of the symptoms, to a level at which the clinical endpoint is maintained or the improved condition is retained.

It will, of course, be understood that the oral administration of IFNτ in accord with the invention may be used in combination with other therapies. For example, IFNτ can be accompanied by administration of an antigen against which an autoimmune response is directed. Examples include co-administration of myelin basic protein and IFNτ to treat multiple sclerosis; collagen and IFNτ to treat rheumatoid arthritis, and acetylcholine receptor polypeptides and IFNτ to treat myasthenia gravis.

Furthermore, IFNτ may be orally administered with known immunosuppressants, such as steroids, to treat autoimmune diseases such as multiple sclerosis. The immunosuppressants may act synergistically with IFNτ and result in a more effective treatment that could be obtained with an equivalent dose of IFNτ or the immunosuppressant alone. More generally, IFNτ administered in combination with drugs, i.e., therapeutic agents, for treatment of autoimmune conditions is contemplated, where representative drugs include, but are not limited to azathioprine, cyclophosphamide, corticosteroids (prednisone, prednisolone, others), cyclosporine, mycophenolate mofetil, antithymocyte globulin, muromonab-CD3 monoclonal antibody, mercaptopurine, mitoxantrone, glatiramer acetate (Copaxone), interferon-beta (Avonex™, Betaseron™, Ribif™), daclizumab, methotrexate, sirolimus, tacrolimus, and others.

Similarly, in a treatment for a cancer or viral disease, IFNτ may be administered in conjunction with, e.g., a therapeutically effective amount of one or more chemotherapy agents. Exemplary types of agents for treatment of cellular proliferative conditions include, but are not limited to, nitrogen mustards, ethylenimines, methylmelamines, alkyl sulfonates, nitrosoureas, triazenes, folic acid anlogs, pyrimidine analogs, purine analogs, vinca alkaloids, epipodphyllotoxins, antibiotics, enzymes, biological response modifiers (e.g., cytokines), platinum coordination complexes, anthracenedione, substituted ureas, methylhydrazine derivatives, adrenocortical suppressants, progestins, estrogens, antiestrogens, androgens, antiandrogens, and gonadotropin releasing hormone anlogs. Representative drugs include, but are not limited to mechlorethamine, cyclophosphamide, ifosfamide, melphalan, chlorambucil, hexamethylmelamine, thiotepa, busulfan, carmustine, lomustine, semustine, streptozocin, dacarbazine, methotrexate, fluorouracil, floxuridine, cytarabine, mercaptopurine, thioguanine, pentostatin, vinblastine, vincristine, etoposide, teniposide, dactinomycin, daunorubicin, doxorubicin, bleomycin, plicamycin, mitomycin, asparaginase, interferon-alpha, cisplatin, carboplatin, mitoxantrone, hydroxyurea, procarbazine, mitotane, aminoglyethimide, prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, zidovudine (AZT), leucovorin, melphalan, cyclophosphamide, dacarbazine, dipyridamole, and others.

Exemplary agents for co-administration with IFNτ for treatment of a viral infection include, but are not limited to, antiherpesvirus agents, antiretroviral agents, and antiviral agents. Representative drugs include acyclovir, famciclovir, foscarnet, ganciclovir, idoxuridine, sorivudine, trifluridine, valacyclovir, vidarabine, didanosine, stavudine, zalcitabine, zidovudine, amantadine, interferon-alpha, ribavirin, rimantadine, lamivudine, protease inhibitors, acyclic nucleoside phosphonates, and others.

IV. EXAMPLES

The following examples further illustrate the invention described herein and are in no way intended to limit the scope of the invention.

Materials and Methods

A. Production of IFNτ

In one embodiment, a synthetic IFNτ gene was generated using standard molecular methods (Ausubel, et al., supra, 1988) by ligating oligonucleotides containing contiguous portions of a DNA sequence encoding the IFNτ amino acid sequence. The DNA sequence used may be either SEQ ID NO:1 or SEQ ID NO:4 or the sequence as shown in Imakawa, K. et al, *Nature*, 330:377–379, (1987). The resulting IFNτ polynucleotide coding sequence may span position 16 through 531: a coding sequence of 172 amino acids.

In one embodiment, the full length synthetic gene StuI/SStI fragment (540 bp) may be cloned into a modified pIN III omp-A expression vector and transformed into a competent SB221 strain of *E. coli*. For expression of the IFNτ protein, cells carrying the expression vector were grown in L-broth containing ampicillin to an OD (550 nm) of 0.1–1, induced with IPTG (isopropyl-1-thio-b-D-galactoside) for 3 hours and harvested by centrifugation. Soluble recombinant IFN-τ may be liberated from the cells by sonication or osmotic fractionation.

For expression in yeast, the IFNτ gene may amplified using polymerase chain reaction (PCR; Mullis, K. B., U.S. Pat. No. 4,683,202, issued 28 Jul. 1987; Mullis, K. B., et al., U.S. Pat. No. 4,683,195, issued 28 Jul. 1987) with PCR primers containing StuI and SacI restriction sites at the 5' and 3' ends, respectively. The amplified fragments were digested with StuI and SacI and ligated into the SacII and SmaI sites of pBLUESCRIPT+(KS), generating pBSY-IFNτ. Plasmid pBSY-IFNτ was digested with SacII and EcoRV and the fragment containing the synthetic IFNτ gene was isolated. The yeast expression vector pBS24Ub (Ecker, D. J., et al., *J. Biol. Chem.* 264:7715–7719 (1989)) was digested with SaII. Blunt ends were generated using T4 DNA polymerase. The vector DNA was extracted with phenol and ethanol precipitated (Sambrook, J., et al., in *MOLECULAR CLONING: A LABORATORY MANUAL*, Second Edition, Cold Spring Harbor Laboratory, Cold Spring Harbor, N.Y. (1989)). The recovered plasmid was digested with SacII, purified by agarose gel electrophoresis, and ligated to the SacII-EcoRV fragment isolated from pBSY-IFNτ. The resulting recombinant plasmid was designated pBS24Ub-IFNτ.

The recombinant plasmid pBS24Ub-IFNτ was transformed into *E. coli*. Recombinant clones containing the IFNτ insert were isolated and identified by restriction enzyme analysis. IFNτ coding sequences were isolated from pBS24Ub-IFNτ and cloned into a *Pichia pastoris* vector containing the alcohol oxidase (AOX1) promoter (Invitrogen, San Diego, Calif.). The vector was then used to transform *Pichia pastoris* GS115 His⁻ host cells and protein was expressed following the manufacturer's instructions. The protein was secreted into the medium and purified by successive DEAE-cellulose and hydroxyapatite chromatography to electrophoretic homogeneity as determined by SDS-PAGE and silver staining.

B. Antiviral Assay to Determine Specific Antiviral Activity

Antiviral activity was assessed using a standard cytopathic effect assay (Familletti, P. C., et al., *Methods in Enzymology*, 78:387–394 (1981); Rubinstein, S. et al., *J. Virol.*, 37:755–758 (1981)). Briefly, dilutions of IFNτ were incubated with Madin-Darby bovine kidney (MDBK) cells for 16–18 hours at 37° C. Following incubation, inhibition of viral replication was determined in a cytopathic effect assay using vesicular stomatitis virus as challenge. One antiviral unit (U) caused a 50% reduction in destruction of the monolayer. For the studies described herein, the IFNτ had a specific activity of about $1 \times 10^8$ antiviral U/mg protein.

Example 1

Administration of IFNτ to Multiple Sclerosis Patients

Humans suffering from multiple sclerosis were enrolled in a trial for treatment with IFNτ. Fifteen patients were randomized into three treatment groups: Group I patients were given IFNτ orally at a dosage of 0.2 mg per day ($2 \times 10^7$ U/day) Group II patients were given IFNτ orally at a dosage of 0.8 mg per day ($8 \times 10^7$ U/day); and Group III patients were given IFNτ orally at a dosage of 1.8 mg per day ($1.8 \times 10^8$ U/day).

Prior to treatment with IFNτ, on screening Day and Day 1 (one), a blood sample was taken from each subject to determine a baseline serum cytokine concentration. Treatment was initiated by administering IFNτ orally to each patient following the blood draw on Day 1. Prior to administration, the vials of IFNτ (SEQ ID NO:3) and syringes were kept in a refrigerator maintained at 2 to 8° C. Prior to self-administration of medication, the patient removed one vial and one syringe from the refrigerator. The cap was removed from the tip of the syringe and the tip of the syringe was placed into the bottle of medication to withdraw the appropriate volume into the syringe as instructed at the clinic on Day 1. The tip of the syringe was placed in the mouth and the syringe contents were emptied into the mouth by depressing the plunger. The patient then swallowed, and if desired, was allowed to drink a glass of water. The patient noted on his/her diary card the date and time the dose was administered.

Blood samples were taken from each patient on Days 1, 4, 8, 15, 29, and 57 of the study. The samples were analyzed for IL-10 concentrations and IFN-γ concentrations by using commercially available ELISA kits (Genzyme, Cambridge, Mass). The results are shown in FIGS. 1A–1D (IL-10) and FIGS. 2A–2D (IFNγ) as well as FIGS. 3A–3E (IL-10 and IFN-γ).

A. Statistical Analysis of Results

Fifteen patients with Relapsing-Remitting Multiple Sclerosis were treated with oral IFN-tau at one of three doses (0.2 mg, 0.6 mg and 1.8 mg) once per day for four weeks. Serum samples were obtained at screening and Days 1, 4, 8, 15, 29 and 57 and assessed for IL-10 and IFN-gamma levels (pg/ml). The results for the three groups were assessed over time using the Repeated Measures Analysis of Variance statistic. Of the 90 data points (Day 1–Day 57), the values for nine missing data points were imputed by carrying the previous values forward.

IL-10:

The analysis found no significant difference between the three dose groups (F=2.92, P=0.0927), no significant effect of time (F=0.70, P=0.6285), and no significant group-by-time interaction (F=0.74, P=0.6803). This suggests IL-10 levels were unchanged following the administration of IFNτ in all three groups across the 28-day dosing period and 28-day follow-up period. The average change from Day 1 to Day 29 of dosing for the lowest to highest dose groups was 7%, 3% and −25%, respectively. The average change to Day 57 for the three dose groups was 10%, −10% and −39%, respectfully. In all cases, the data in all three groups was highly variable.

IFN-γ:

The analysis found no significant difference between the three dose groups (F=1.06, P>0.3769), no significant effect of time (F=1.86, P=0.1140), and no significant group-by-time interaction (F=1.45, P=0.1820). This suggests IFN-γ levels were unchanged following the administration of IFNτ in all three groups across the 24-day dosing period and 28-day follow-up period. The average change from Day 1 to Day 29 of dosing for the lowest to highest dose groups was −63%, −14% and 35%, respectively. The average change to Day 57 for the three dose groups was −27%, −46% and 22%, respectfully. Similar to the IL-10 analysis, the data in all three groups was highly variable.

Example 2

Administration of IFNτ Three Times Daily to Human Patients Infected with Hepatitis C A. IFNτ Preparation On day one, one bottle of IFNτ (SEQ ID NO:3) was removed from the refrigerator and the patient self-administered the proper volume of test material according to Table 2. IFNτ (SEQ ID NO:2) may also be prepared and administered in the same manner.

TABLE 2

Recombinant Ov-IFNτ Patient Dose Administration

| Dose Group | Number of Patients | IFNτ (mg/mL) | Volume (mL) per Dose (TID) | Total Daily Dose (mg) | Total Daily Dose (U) |
|---|---|---|---|---|---|
| I | 6 | 1.0 | 0.33 | 1.0 | $1 \times 10^8$ |
| II | 6 | 1.0 | 1.0 | 3.0 | $3 \times 10^8$ |
| III | 6 | 1.0 | 3.0 | 9.0 | $9 \times 10^8$ |

B. Patient Dosing Instructions

All vials of test material and syringes were kept in a refrigerator maintained at 2 to 8° C. Prior to the self-administration of medication, the patient removed one vial and one syringe from the refrigerator. The cap was removed from the tip of the syringe and the tip of the syringe was placed into the bottle of medication to withdraw the appropriate volume into the syringe as instructed at the clinic on Day 1.

The tip of the syringe was placed in the mouth and the syringe contents were emptied into the mouth by depressing the plunger. The patient then swallowed the test material. If desired, the patient was allowed to drink a glass of water. The patient noted on his/her diary card the date and time the dose of test material was administered.

The above steps were repeated three times per day at approximately eight-hour intervals: once in the morning, once at midday, and once in the evening.

C. Results

Blood samples were taken at defined intervals over a 169 day test period. The samples were analyzed for IL-10 levels and IFN-γ levels in the serum using ELISA kits (Genzyme, Cambridge, Mass.) following the manufacturer's instructions. The viral titer of hepatitis C, using reverse-transcriptase polymerase chain reaction, blood levels of 2',5'-oligoadenylate synthetase (OAS), and the serum concentration of alanine aminotransferase (ALT) were also determined and are not reported here.

The results for each subject are shown in FIGS. 4A–4D (IL-10 levels) and FIGS. 5A–5D (IFN-γ levels), and in FIGS. 6A–6F (IL-10 and IFN-γ).

D. Statistical Analysis of Results

The results for the three groups were assessed over time using the Repeated Measures Analysis of Variance statistic. The data for one patient in Group II was not used because of missing baseline serum samples. Of the 204 data points (Day 1–Day 169), the values for seven missing data points for both measures were imputed by carrying the previous values forward.

IL-10: The analysis found a statistical significant difference between the three groups (F=12.08, P=0.0009), a significant effect of time (F=11.20, P=0.0001) and a significant group-by-time interaction (F=7.88, P=0.001). The latter finding is clearly seen by the difference in IL-10 response rates between the three dose groups over time. While the lowest dose group (Group I; 0.33 mg TID) produced a 22% increase in IL-10 levels from Day 1 to Day 43, Group II (1 mg TID) produced a peak response of 114% by Day 29. In contrast, Group III (3 mg TID) produced a 387% increase by Day 43 with a peak of 484% by Day 71.

The significant interaction term is also supported by the differential decline between dose groups in IL-10 levels once dosing was terminated at Day 84: Group I declined from its 11% gain at Day 85 to 4% at Day 169, and Group II declined from 95% to 0.5% over the same time period. Therefore the two lowest dose groups returned to baseline six months following the termination of dosing. The highest dose group (Group III; 3 mg TID), however, declined from 453% to 194% by Day 169, thus still showing a substantial increase over baseline six months after dosing was stopped.

IFN-γ: The analysis found no significant difference between the three dose groups (F=1.13, P>0.3499), no significant effect of time (F=1.55, P=0.1187), and no significant group-by-time interaction (F=1.39, P=0.1275). This indicates IFN-γ levels were not significantly changed following the administration of IFNτ in all three groups across the 84-day dosing period and 84-day follow-up period. The average change from Day 1 to Day 85 of dosing for the lowest to highest dose groups was −6%, 8% and 7%, respectively. Interestingly, the average change to Day 169 for the three dose groups was 4%, 21% and 31%, respectfully, suggesting a dose response following the termination of dosing.

Example 3

Administration of IFNτ Twice Daily to Patients Infected with Hepatatis C

Five patients infected with hepatitis C were recruited for a study. The patients were treated with IFNτ according to the method of Example 2, each patient received 7.5 mg twice daily, for a total daily dose of 15 mg ($1.5 \times 10^9$ U). The first dose was taken in the morning, before breakfast. The second dose was taken at least three hours after an evening meal.

Blood samples were taken at defined intervals over the 113 day test period. The samples were analyzed for IL-10, IL-12, and IFN-γ levels in the serum using commercially available ELISA kits (Genzyme, Cambridge, Mass.). The results are shown in FIG. 7A (IL-10), FIG. 7B (IFNγ), and in FIGS. 8A–8D (IL-10, IL-12, and IFN-γ) for each of the five patients Although the invention has been described with respect to particular embodiments, it will be apparent to those skilled in the art that various changes and modifications can be made without departing from the invention.

The invention claimed is:

1. A method for treating multiple sclerosis in a human subject, comprising:
   orally administering interferon-tau to the subject at a daily dosage of about 1×10$^9$ Units or more, and
   continuing to orally administer interferon-tau to the subject at said daily dose until a desired clinical endpoint is achieved.

2. The method of claim 1, wherein said administering comprises administering an interferon-tau selected from ovine interferon-tau and bovine interferon-tau.

3. The method of claim 2, wherein said administering comprises administering ovine interferon-tau having a sequence identified as SEQ ID NO:2 or SEQ ID NO:3.

4. The method of claim 1, wherein said orally administering comprises orally administering a dosage form for release of interferon-tau to the intestinal tract of the subject.

5. The method of claim 1, further comprising administering a second therapeutic agent to the subject.

6. The method of claim 5, wherein said second therapeutic agent is an agent suitable for treatment of multiple sclerosis.

* * * * *